United States Patent
Banks et al.

(10) Patent No.: US 6,670,362 B2
(45) Date of Patent: Dec. 30, 2003

(54) PYRIDAZINE ENDOTHELIN ANTAGONISTS

(75) Inventors: Bernard Joseph Banks, County of Kent (GB); Anthony Logan Chubb, County of Kent (GB); Douglas James Critcher, County of Kent (GB); James John Eshelby, County of Kent (GB); Darren John Schulz, Groton, CT (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 09/951,019

(22) Filed: Sep. 12, 2001

(65) Prior Publication Data

US 2002/0061889 A1 May 23, 2002

Related U.S. Application Data

(60) Provisional application No. 60/239,747, filed on Oct. 12, 2000.

(30) Foreign Application Priority Data

Sep. 20, 2000 (GB) .............................................. 0023074

(51) Int. Cl.[7] .......................... A61K 31/501; A61P 9/10; C07D 403/04
(52) U.S. Cl. .................................. 514/252.02; 544/238
(58) Field of Search ...................... 514/252.02; 544/238

(56) References Cited

U.S. PATENT DOCUMENTS

| | | | | |
|---|---|---|---|---|
| 4,698,091 A | * | 10/1987 | Brunner et al. ................. | 71/87 |
| 5,104,877 A | | 4/1992 | Boger .......................... | 31/505 |
| 5,147,876 A | | 9/1992 | Mitzuchi et al. ............... | 31/505 |
| 5,166,206 A | | 11/1992 | Allen et al. .................... | 31/505 |
| 5,270,313 A | | 12/1993 | Burri et al. ................... | 514/252 |
| 5,292,740 A | | 3/1994 | Burri et al. .................... | 403/4 |
| 5,420,129 A | | 5/1995 | Breu et al. .................... | 514/252 |
| 5,541,186 A | | 7/1996 | Breu et al. .................... | 31/505 |
| 5,559,081 A | | 9/1996 | Gates et al. ................... | 239/32 |
| 5,589,478 A | | 12/1996 | Yamada et al. ............... | 239/32 |
| 5,707,966 A | * | 1/1998 | Schacht et al. ................ | 514/19 |
| 5,728,706 A | | 3/1998 | Yamada et al. ................ | 401/2 |
| 5,739,333 A | | 4/1998 | Yamada et al. ............. | 544/296 |
| 5,837,708 A | | 11/1998 | Breu et al. .................... | 239/69 |
| 5,856,484 A | | 1/1999 | Breu et al. .................... | 239/47 |
| 5,861,401 A | | 1/1999 | Bradbury ....................... | 43/58 |
| 5,883,090 A | * | 3/1999 | Dorsch et al. ............... | 514/222 |
| 5,883,092 A | | 3/1999 | Hirata et al. ................... | 413/4 |
| 5,962,682 A | | 10/1999 | Breu et al. ................... | 311/21 |
| 6,004,965 A | | 12/1999 | Breu et al. .................... | 43/54 |
| 6,008,224 A | | 12/1999 | Hirata et al. ................... | 401/4 |
| 6,083,951 A | | 7/2000 | Bradbury ....................... | 43/54 |
| 6,083,955 A | | 7/2000 | Harada et al. ............... | 514/269 |
| 6,133,442 A | | 10/2000 | Breu et al. ................... | 213/75 |

FOREIGN PATENT DOCUMENTS

| | | | |
|---|---|---|---|
| EP | 0713875 | 11/1995 | ......... C07D/409/12 |
| EP | 0801062 | 10/1997 | ......... C07D/239/52 |
| EP | 0815861 | 1/1998 | ......... A61K/31/505 |
| EP | 0852226 | 8/1998 | ......... C07D/239/48 |
| EP | 0716649 | 9/1998 | ......... C07D/209/04 |
| EP | 0882719 | 12/1998 | ......... C07D/239/46 |
| EP | 0959072 | 11/1999 | ......... C07D/239/69 |
| EP | 0959073 | 11/1999 | ......... C07D/239/69 |
| EP | 0979822 | 2/2000 | ......... C07D/401/04 |
| WO | WO9506636 | 3/1995 | ......... C07D/209/04 |
| WO | WO9510506 | 4/1995 | ......... C07D/239/42 |
| WO | WO9619455 | 6/1996 | ......... C07D/213/46 |
| WO | WO9619459 | 6/1996 | ......... C07D/239/69 |
| WO | WO9626196 | 8/1996 | ......... C07D/295/116 |
| WO | WO9803488 | 7/1997 | ......... C07D/239/34 |
| WO | WO9749400 | 12/1997 | .......... A61K/31/44 |
| WO | WO9824782 | 6/1998 | ......... C07D/401/04 |
| WO | WO9857934 | 12/1998 | ......... C07D/213/79 |
| WO | WO9857938 | 12/1998 | ......... C07D/239/46 |
| WO | WO9906371 | 2/1999 | ......... C07D/213/82 |
| WO | WO9912908 | 3/1999 | ......... C07D/215/42 |
| WO | WO9932117 | 7/1999 | .......... A61K/31/44 |
| WO | WO9950249 | 10/1999 | ......... C07D/239/48 |
| WO | WO9950255 | 10/1999 | ......... C07D/249/00 |
| WO | WO0006568 | 2/2000 | ......... C07D/471/04 |

OTHER PUBLICATIONS

H. Arai, et al., *Nature*, 348, 730 (1990).
A. Tahara, et al., *Metabolism Clinical and Experimental*, 40, 1235 (1991).
S. Douglas, et al., *Journal of Cardiovascular Pharmacology*, 22 (Suppl. 8), 371 (1993).
S. Douglas, et al., *Circulation Research*, 75 (1994).
H. Krum, et al., *New England Journal of Medicine*, 338, 784–790 (1998).

(List continued on next page.)

*Primary Examiner*—Richard L. Raymond
*Assistant Examiner*—Tamthom N. Truong
(74) *Attorney, Agent, or Firm*—Peter C. Richardson; Gregg C. Benson; B. Timothy Creagan

(57) ABSTRACT

Compounds of formula (I), pharmaceutical formulations thereof and the use of such compounds for treating endothelin mediated diseases or conditions are described herein.

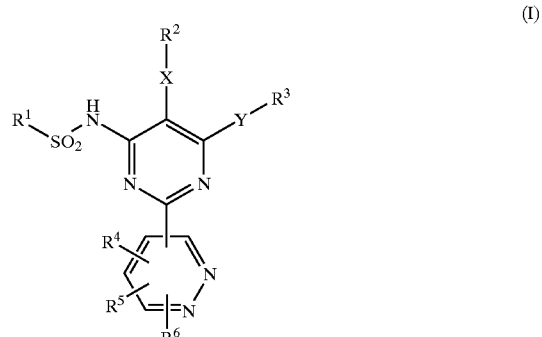

The compounds of the present invention have affinity for endothelin receptors, are selective for $ET_A$ over $ET_B$, and thus are useful in the treatment of conditions mediated by endothelin.

35 Claims, No Drawings

OTHER PUBLICATIONS

Strachan, *Hypertension,* 33, 581–585 (1999).
Y. Saita, et al., *European Journal of Pharmacology,* 349, 123–128 (1988).
R. K. Nikolov, et al., *Drugs of Today,* 28(5), 303 (1992).
Benamou, *Pulmonary Pharmacology & Therapeutics,* 11, 231–235 (1998).
Redington, *American Journal of Respiratory and Critical Care Medicine,* 151, 1034–1039 (1995).
F. Stockenhuber, et al., *Clinical Science,* 82,255 (1992).
M. Yasuda, et al., *American Heart Journal,* 119,801 (1990).
J. T. Stewart, et al., *Br. Heart Journal,* 66, 7 (1991).
D. J. Stewart, et al., *Annals of Internal Medicine,* 114,464 (1991).
B. A. Clark, et al., *Am J Obstet Gynecol.* 166,962 (1992).
A. Collier, et al., *Diabetes Care,* 15(8), 1038 (1992).
S. H. Murch, et al., *Lancet,* 339,381 (1982).
A. Lerman, et al., *New England Journal of Medicine,* 325,997 (1991).
R.J. Rodeheffer, et al., *Am. J. Hypertension* 4, 9A (1991).
K. Tomita et al., Med. Philos., vol. 13, No. 1, p. 6466 (1994).
Japanese Patent No. 10226649 Derwent Abstract Only.
Japanese Patent No. 10194972 Derwent Abstract Only.
Japanese Patent No. 09059160 Derwent Abstract Only.
Japanese Patent No. 2000007661 Japanese Translations from the Japanese Patent Office.
Japanese Patent No. 11043482 Japanese Translations from the Japanese Patent Office.
Japanese Patent No. 09067370 Japanese Translations from the Japanese Patent Office.
Japanese Patent No. 09067352 Japanese Translations from the Japanese Patent Office.
Japanese Patent No. 08283119 Japanese Translations from the Japanese Patent Office.
Japanese Patent No. 4001192 Japanese Translations from the Japanese Patent Office.
Japanese Patent No. 2000143637 Japanese Translations from the Japanese Patent Office.

* cited by examiner

PYRIDAZINE ENDOTHELIN ANTAGONISTS

This application claims the benefit of U.S. Provisional Patent Application No. 60/239,747 filed Oct. 12, 2000 and incorporated herein by reference.

FIELD OF THE INVENTION

This invention relates to pyridazine derivatives useful in the treatment of a variety of conditions mediated by endothelin and to pharmaceutical formulations containing such compounds useful for the treatment of human and non-human mammals.

BACKGROUND

Endothelin (ET) is a potent vasoconstrictor synthesized and released by endothelial cells. There are three distinct isoforms of ET: ET-1, ET-2 and ET-3, all being 21-amino acid peptides and herein the term 'endothelin' refers to any or all of the isoforms. Two receptor subtypes, $ET_A$ and $ET_B$ have been pharmacologically defined (see for example H. Arai et al., Nature, 348, 730, 1990) and further subtypes have recently been reported. Stimulation of $ET_A$ promotes vasoconstriction and stimulation of $ET_B$ receptors causes either vasodilation or vasoconstriction. The main effects of ET are observed in the cardiovascular system, particularly in the coronary, renal, cerebral and mesenteric circulation, and the effects of endothelin are often long-lasting. Stimulation of ET receptors also mediate further biological responses in cardiovascular and non-cardiovascular tissues such as cell proliferation and matrix formation.

Increased circulating levels of endothelin have been observed in patients who have undergone percutaneous transluminal coronary angioplasty (PTCA) (A. Tahara et al., Metab. Clin. Exp., 1991, 40,1235) and ET-1 has been found to induce neointimal formation in rats after balloon angioplasty (S. Douglas et al., J. Cardiovasc. Pharm., 1993, 22 (Suppl 8), 371). The same workers have found that an endothelin antagonist, SB-209670, causes a 50% reduction in neointimal formation relative to control animals (S. Douglas et al., Circ. Res., 1994, 75). Antagonists of the endothelin receptor may thus be useful in preventing restenosis post PTCA. The $ET_{A/B}$ receptor antagonist Bosentan reportedly decreased blood pressure in hypertensive patients (H. Krum et al., New Eng. J. Med., 1998, 338, 784–790). Antagonists of $ET_B$ receptors such as BQ-788 have been demonstrated to increase peripheral resistance in man (Hypertension, 1999, 33, 581–585). Thus $ET_A$-selective receptor antagonists are of benefit in hypertension.

Endothelin-1 is produced in the human prostate gland and endothelin receptors have been identified in this tissue (Y. Saita et al., Eur. J. Pharmacol., 1988, 349,123–128). Since endothelin is a contractile and proliferative agent, endothelin antagonists are useful in the treatment of benign prostate hypertrophy.

There is widespread localization of endothelin and its receptors in the central nervous system and cerebrovascular system (R. K. Nikolov et al., Drugs of Today, 1992, 28(5), 303) with ET being implicated in cerebral vasospasm, cerebral infarcts, septic shock, myocardial infarction and neuronal death.

Elevated levels of endothelin have also been observed in patients with: recurrent airway obstruction (Pulm. Pharm. Ther., 1998, 11: 231–235); asthma (Am. J. Resp. Crit. Care Med., 1995, 151:1034–1039); acute renal failure (K. Tomita et al., Med. Philos., 1994, 13(1), 64–66); chronic renal failure (F. Stockenhuber et al., Clin. Sci. (Lond.), 1992, 82, 255); ischemic Heart Disease (M. Yasuda, Am. Heart J., 1990, 119, 801); stable or unstable angina (J. T. Stewart, Br. Heart J., 1991, 66, 7); pulmonary hypertension (D. J. Stewart et al., Ann. Internal Medicine, 1991, 114, 464); congestive heart failure (R. J. Rodeheffer et al., Am. J. Hypertension, 1991, 4, 9A); preeclampsia (B. A. Clark et al., Am. J. Obstet. Gynecol., 1992, 166, 962); diabetes (A. Collier et al., Diabetes Care, 1992, 15 (8), 1038); Crohn's disease (S. H. Murch et al., Lancet, 1992, 339, 381); and atherosclerosis (A. Lerman et al., New Eng. J. Med., 1991, 325, 997).

In every case the disease state associated with the physiologically elevated levels of endothelin is potentially treatable with a substance which decreases the effect of endothelin, such as an endothelin receptor antagonist, or a compound which binds endothelin such that it reduces the effective concentration thereof at the endothelin receptors.

Compounds that antagonise the $ET_A$ receptor to a greater extent than the $ET_B$ receptor are preferred as $ET_A$ receptors are predominantly present in vascular smooth muscles. Blockade of $ET_B$ receptor activation may reverse endothelial dependent vasodilation which is beneficial in hypertension. ET may also mediate regeneration of damaged tissue via the $ET_B$ receptor, such as proximal tubule cells in the kidney. Thus blockade of $ET_B$ receptors, e.g. with a non-selective ET antagonist could inhibit tissue repair. $ET_B$ receptors are also involved in the clearance of ET from the systemic circulation. Increased levels of ET are generally considered detrimental. Rises in circulating levels have been observed with non-selective ET antagonists. Treatment with selective $ET_A$ receptor antagonists are not likely to induce such rises in circulating levels.

There are a number of publications relating to N-(pyrimidin-4-yl) sulfonamide derivatives having endothelin binding/antagonist activity, for example EP-A-0743307, EP-A-0658548, EP-A-0633259, EP-A-0882719, WO-A-96/20177, EP-A-0801062, WO-A-97/09318, EP-A-0852226, EP-A-0768304, WO-A-96/19459, WO-A-98/03488, EP-A-0601386, EP-A-0510526 and EP-A-0713875.

Various N-4-pyrimidinyl sulfonamide derivatives possessing endothelin antagonist activity are described in JP-A-09059160, JP-A-10194972 and JP-A-10226649.

International Patent Application publication number WO-A-96/19455 discloses phenyl and pyridin-4-yl sulfonamides as endothelin antagonists.

SUMMARY OF THE INVENTION

According to the present invention, there are provided compounds of formula (I)

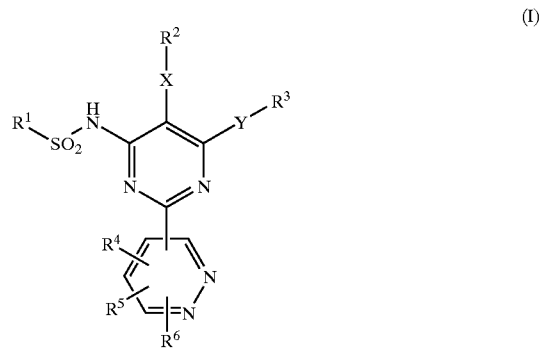

wherein $R^1$ is $(CR^7R^8)_n-(C_3-C_8)$cycloalkyl, $(CR^7R^8)_n-$ heterocycle, $(CR^7R^8)_n$-(benzofused heterocycle), $(CR^7R^8)_n$-aryl, $NR^9R^{10}$, $(CR^7R^8)_n$-heteroaryl, and $(CR^7R^8)_n$-(benzofused heteroaryl), where $R^7$ and $R^8$ are each independently H or $(C_1-C_6)$alkyl, $R^9$ and $R^{10}$ are each independently H or $(C_1-C_6)$alkyl optionally substituted by aryl, heterocycle, benzofused heterocycle, heteroaryl, benzofused heteroaryl, or $(C_3-C_8)$cycloalkyl, and n is 2, 3, 4, 5, or 6;

$R^2$ is (a) phenyl optionally fused with a heterocycle, benzofused heterocycle, heteroaryl, or benzofused heteroaryl, (b) naphthyl optionally fused with a heterocycle, benzofused heterocycle, heteroaryl, or benzofused heteroaryl, or (c) heteroaryl or benzofused heteroaryl, where groups (a), (b) and (c) are optionally substituted by $(C_1-C_6)$alkyl, $(C_1-C_6)$alkoxy, halo, unsubstituted heterocycle, unsubstituted benzofused heterocycle, unsubstituted heteroaryl, unsubstituted benzofused heteroaryl, phenyl, naphthyl, $CO_2R^{11}$, $OC(O)R^{11}$, $CONR^{11}R^{12}$, or $S(O)_pR^{11}$, where p is 0, 1, or 2, and $R^{11}$ and $R^{12}$ are each independently H or $(C_1-C_6)$alkyl;

$R^3$ is (e) $(C_1-C_6)$alkyl, (f) $(C_2-C_6)$alkenyl, (g) $(C_2-C_6)$ alkynyl, or (h) $(C_3-C_8)$cycloalkyl, where groups (e), (f), (g) and (h) are optionally substituted by $OR^{11}$, halo, $NHC(O)(C_1-C_6)$alkyl, O-heterocycle, O-(benzofused heterocycle), O-heteroaryl, O-(benzofused heteroaryl), OC(O)NH-heterocycle, OC(O)NH-(benzofused heterocycle), OC(O)NH-heteroaryl, OC(O)NH-(benzofused heteroaryl), $NH_2$, NHC(O)O-heteroaryl, NHC(O)O-(benzofused heteroaryl), NHC(O)NH-heteroaryl, or NHC(O)NH-(benzofused heteroaryl);

X is O, NH, a direct link, or $S(O)_p$, where p is 0, 1 or 2;

Y is O, NH, or $S(O)_p$, where p is 0, 1 or 2; and $R^4$, $R^5$ and $R^6$ are each independently selected from the group consisting of H, halo, heterocycle, benzofused heterocycle, heteroaryl, benzofused heteroaryl, aryl, $(C_1-C_6)$alkoxy, $(C_1-C_6)$alkyl optionally substituted by halo, $OR^9$ or $NH_2$, and $S(O)_pR^9$, where p is 0, 1 or 2;

a pharmaceutically acceptable salt thereof, a prodrug of the compound or salt, a solvate or the compound, salt or prodrug, or a polymorph of the compound, salt, prodrug, or solvate. Processes for making compounds of formula (I) and key intermediates are also provided and described in more detail below.

In another embodiment of the present invention, a pharmaceutical composition is provided comprising (a) a compound of the present invention; and (b) a pharmaceutically acceptable diluent, carrier or adjuvant.

In yet another embodiment of the present invention, a method for treating a condition or disease mediated by an endothelin receptor (in particular, an $Et_A$ receptor) is provided comprising the step of administering to a patient in need of such treatment a therapeutically-effective amount of a compound of the present invention. In particular, the method is useful for the prevention or treatment of conditions or diseases selected from the group consisting of restenosis, acute or chronic renal failure, pulmonary hypertension, systemic hypertension, benign prostatic hyperplasia, male erectile dysfunction, prostate cancer, metastatic bone cancer, congestive heart failure, stroke, subarachnoid haemorrhage, angina, atherosclerosis, cerebral and cardiac ischemia, prevention of ischaemia or reperfusion injury, cyclosporin induced nephrotoxicity, glaucoma, radiocontrast nephropathy, diabetic neuropathy, allergy, restoration of organ perfusion in haemorrhagic shock, lipoprotein lipase related disorders, chronic obstructive pulmonary disease and hyaline membrane disease in newborn.

Definitions

As used herein, the term "alkyl" is defined as a hydrocarbon radical of the general formula $C_nH_{2n+1}$. The alkane radical may be straight or branched. For example, the term "$(C_1-C_6)$alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, 1,1-dimethylpropyl, neopentyl, 3,3-dimethylpropyl, n-hexyl, 2-methylpentyl, 2-ethylbutyl, 3-methylpentyl, 3-ethylbutyl, 4-methylpentyl, and other constitutional isomers containing 1 to 6 carbon atoms (including stereoisomers). The alkane radical may be unsubstituted or substituted with one or more substituents. For example, a "halo-substituted alkyl" refers to an alkyl group substituted with one or more halogen atoms (e.g., fluoromethyl, difluoromethyl, trifluoromethyl, perfluoroethyl, chloromethyl, bromomethyl, and the like). Similarly, the alkyl portion of an alkoxy, alkenyl or alkynyl group has the same meaning as alkyl defined above.

The term "cycloalkyl" refers to a fully hydrogenated nonaromatic carbocyclic ring where a hydrogen has been removed from one of the ring carbons. For example, $(C_3-C_6)$cycloalkyl includes groups such as cyclopropyl, cyclobutyl, cyclopentyl, and cyclohexyl.

The term "aryl" is defined as a single or multi-carbocyclic aromatic ring system where a hydrogen has been removed from the ring position of the arene nucleus. A multicyclic aromatic ring system may be fused (e.g., naphthyl) or non-fused (e.g., biphenyl). Unless specified otherwise, the ring system contains six to fourteen cyclic conjugated carbon atoms. Suitable aryl groups include phenyl, naphthyl, azulyl, anthryl, phenanthryl, benz[a]anthryl, and biphenyl. The aryl groups may be unsubstituted or substituted with one or more substituents (typically, 1 to 3 substituents). Suitable substituents include halo, $CO_2R^9$, $OCOR^9$, OH, $het^4$, $S(O)_pR^{11}$, $(C_1-C_6)$alkoxy, or $(C_1-C_6)$alkyl optionally substituted by OH, $(C_1-C_6)$alkoxy or halo.

The term heterocycle is defined as a fully saturated or partially unsaturated, single or multicyclic ring system wherein one or more of the rings contains 1–3 heteroatoms, each independently selected from N, O and S, and where a hydrogen has been removed from one of the ring positions of the nucleus. Unless specified otherwise, the heterocyclic ring system contains three to eight members. For example, a "3- to 8-membered heterocycle" includes groups such as epoxy, aziridinyl, 2H-pyrrolyl, 2H-imidazolyl, 1,2-dithiolyl, 1,3-dithiolyl, 3H-1,2-oxathiolyl, 3H-1,2,3-dioxazolyl, 1,2,4-dioxazolyl, 1,3,2-dioxazolyl, 1,3,4-dioxazolyl, 5H-1,2,5-oxathiazolyl, 1,3-oxathiolyl, 2H-pyranyl, 4H-pyranyl, 1,3-dioxinyl, piperazinyl, oxazinyl, isoxazinyl, morpholinyl and the like. The heterocycle may optionally be fused to a benzene ring (referred to herein as "benzofused heterocycle"). For example, a 5- or 6-membered heterocycle fused to a benzene ring includes groups such as 2H-chromenyl, benzoxazinyl, and the like. Unless specified otherwise, the heterocyclic groups or benzofused heterocyclic groups may be substituted with 1 to 3 substitutions selected from the group consisting of halo, $CO_2R^9$, $OCOR^9$, OH, unsubstituted heteroaryl, unsubstituted benzofused heteroaryl, $S(O)_pR^{11}$, $(C_1-C_6)$alkoxy, or $(C_1-C_6)$ alkyl optionally substituted by OH, $(C_1-C_6)$alkoxy or halo).

The term "heteroaryl" is defined as a five- or six-membered aromatic ring system containing 1–3 heteroatoms, each independently selected from N, O and S, where a hydrogen has been removed from one of the ring positions of the nucleus. For example, a 5- or 6-membered heteroaryl group includes furyl, thienyl, pyrrolyl, oxazolyl, thiazolyl, imidazolyl, pyrazolyl, isoxazolyl, isothiazolyl, pyridinyl, pyridiazinyl, pyrimidinyl and pyrazinyl. The heteroaryl group may optionally be fused to a benzene ring (referred to herein as "benzofused heteroaryl"). Examples of 5- or 6-membered heteroaryl groups fused to a benzene ring include indolyl, benzothiophenyl, benzoxazolyl, anthranil, indazolyl, quinolinyl, isoquinolinyl, cinnolinyl, quinazolinyl, and the like. Unless specified otherwise, the heteroaryl groups or benzofused heteroaromatic groups may be substituted with 1 to 3 substitutions selected from the group consisting of halo, $CO_2R^9$, $OCOR^9$, OH, unsubstituted heteroaryl, unsubstituted benzofused heteroaryl, $S(O)_pR^{11}$, $(C_1-C_6)$alkoxy, or $(C_1-C_6)$alkyl optionally substituted by OH, $(C_1-C_6)$ alkoxy or halo).

The term "halo" refers to fluoro, chloro, bromo and iodo groups.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The phrase "pharmaceutically acceptable" indicates that the substance or composition must be compatible chemically and/or toxicologically, with the other ingredients comprising a formulation, and/or the patient being treated therewith.

The terms "treating", "treat", or "treatment" embrace both preventative (i.e., prophylactic) and palliative treatment.

DETAILED DESCRIPTION

We have unexpectedly found that pyridazines of formula (I) above have good affinity for endothelin receptors, and are selective for $ET_A$ over $ET_B$. The compounds of formula (I) may be used per se or as their corresponding pharmaceutically acceptable salt. The salt may be readily prepared by mixing together solutions of a compound of the formula (I) and the desired acid or base, as appropriate. The salt may precipitate from solution and be collected by filtration or may be recovered by evaporation of the solvent. The pharmaceutically acceptable salts of the compounds of the formula (I) include the acid addition and the base salts thereof. Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts. Suitable base salts are formed from bases which form non-toxic salts and examples are the sodium, potassium, aluminium, calcium, magnesium, zinc and diethanolamine salts. For a review on suitable salts see Berge et al, *J. Pharm. Sci.*, 66, 1–19, 1977.

The compounds of the present invention also include pharmaceutically acceptable solvates (including hydrates) of the compounds of the formula (I).

Also included within the scope of the present invention are polymorphs of the compound of formula (I) and polymorphs of the corresponding pharmaceutically acceptable salts and solvates thereof.

It will also be appreciated that the compounds of the invention will include prodrugs thereof: pharmaceutically acceptable derivatives of (I) in which the functional groups explicitly recited above have been derivatized to provide prodrugs which can be converted to the parent compound in vivo. Such prodrugs are discussed in *Drugs of Today, Vol.* 19, 499–538 (1983) and *Annual Reports in Medicinal Chemistry*, Vol. 10, Ch 31 p306–326.

A compound of the formula (I) may contain one or more asymmetric carbon atoms and therefore exists in two or more stereoisomeric forms. Where a compound of the formula (I) contains an alkenyl or alkenylene group, cis/trans (or E/Z) isomerism may also occur. The present invention includes the individual stereoisomers of the compounds of the formula (I) and, where appropriate, the individual tautomeric forms thereof, together with mixtures thereof.

Racemic substances may either be separated using preparative HPLC and a column with a chiral stationary phase or resolved to yield individual enantiomers utilizing methods known to those skilled in the art. In addition, chiral intermediates may be resolved and used to prepare chiral compounds of formula (I).

Preferred compounds of formula (I) are those where the pyrimidine ring is attached at the 3 or 4 position of the pyridazine ring.

Preferably, $R^1$ is $(CR^7R^8)_n$-aryl, $(CR^7R^8)_n$-heteroaryl, $(CR^7R^8)_n$-(benzofused heteroaryl), or $(CR^7R^8)_n-(C_{3-8}$ cycloalkyl) and n is 2, 3, 4, 5 or 6. More preferably, $R^1$ is $(CR^7R^8)_n$-aryl or $(CR^7R^8)_n-(C_3-C_8)$cycloalkyl and n is 2 or 3. Most preferably, $R^1$ is $(CR^7R^8)_n$-aryl or $(CR^7R^8)_n-(C_3-C_8$)cycloalkyl, and n is 2.

Preferably, $R^2$ is phenyl, heteroaryl, or benzofused heteroaryl, each optionally substituted by $(C_1-C_6)$alkyl, $(C_1-C_6)$alkoxy, halo, unsubstituted heterocycle, unsubstituted benzofused heterocycle, unsubstituted heteroaryl, unsubstituted benzofused heteroaryl, phenyl, naphthyl, $CO_2R^{11}$, $OC(O)R^{11}$ or $CONR^{11}R^{12}$. More preferably, $R^2$ is phenyl optionally substituted by $(C_1-C_6)$alkyl, $(C_1-C_6)$ alkoxy, halo, unsubstituted heterocycle, unsubstituted benzofused heterocycle, unsubstituted heteroaryl, unsubstituted benzofused heteroaryl, phenyl, naphthyl, $CO_2R^{11}$, $OC(O)R^{11}$ or $CONR^{11}R^{12}$. Most preferably, $R^2$ is phenyl optionally substituted by $(C_1-C_3)$alkyl, $(C_1-C_3)$alkoxy, F or Cl.

Preferably, $R^3$ is $(C_1-C_6)$alkyl, $(C_2-C_6)$alkynyl or $(C_3-C_8)$cycloalkyl, where the alkyl, alkynyl and cycloalkyl groups are optionally substituted by $OR^{11}$, halo, NHC(O) $C_{1-6}$ alkyl, O-heterocycle, O-(benzofused heterocycle), O-heteroaryl, O-(benzofused heteroaryl), OC(O)NH-heterocycle, OC(O)NH-(benzofused heterocycle), OC(O) NH-heteroaryl, or OC(O)NH-(benzofused heteroaryl). More preferably, $R^3$ is $(C_2-C_3)$alkynyl or $(C_1-C_3)$alkyl (optionally substituted by $OR^{11}$, halo, $NHC(O)(C_1C_{-6})$alkyl, O-heterocycle, O-(benzofused heterocycle), O-heteroaryl, O-(benzofused heteroaryl), OC(O)NH-heterocycle, OC(O) NH-(benzofused heterocycle), OC(O)NH-heteroaryl, or OC(O)NH-(benzofused heteroaryl). Most preferably, $R^3$ is $(C_1-C_3)$alkyl, $CH_2CH_2OH$, $CH_2C\!=\!CH$, $CH_2CH_2F$ or $CH_2CH_2OCH_3$.

Preferably, $R^4$, $R^5$ and $R^6$ are each independently H, $(C_1-C_6)$alkoxy, $S(C_1-C_6)$alkyl, phenyl, halo, heterocycle, benzofused heterocycle, heteroaryl, benzofused heterocycle or $(C_1-C_6)$alkyl optionally substituted by halo or $NH_2$. More preferably, $R^4$ and $R^5$ are each hydrogen and $R^6$ is H, $(C_1-C_6)$alkoxy or $(C_1-C_6)$alkyl optionally substituted by halo. Most preferably, $R^4$ and $R^5$ are each hydrogen and $R^6$ is H or $(C_1-C_6)$alkyl.

Preferably, $R^7$ and $R^8$ are each independently H or $(C_1-C_3)$alkyl. More preferably, $R^7$ and $R^8$ are each independently H or $CH_3$. Most preferably, $R^7$ and $R^8$ are each H.

Preferably, $R^9$ and $R^{10}$ are each independently H or ($C_1$–$C_3$)alkyl optionally substituted by aryl, heterocycle, benzofused heterocycle, heteroaryl, benzofused heteroaryl, or ($C_3$–$C_8$) cycloalkyl. More preferably, $R^9$ and $R^{10}$ are each independently H or ($C_1$–$C_3$)alkyl optionally substituted by aryl, heterocycle, or benzofused heterocycle. Most preferably, $R^9$ and $R^{10}$ are each H.

Preferably, $R^{11}$ and $R^{12}$ are each independently H or ($C_1$–$C_3$)alkyl. More preferably, $R^{11}$ and $R^{12}$ are each independently H or $CH_3$.

Preferably, X is O, NH or a direct link. Most preferably, X is O.

Preferably, Y is O or NH. Most preferably, Y is O.

Preferably, n is 2, 3 or 4. Most preferably, n is 2.

A preferred set of compounds are those described in the Examples and pharmaceutical derivatives thereof.

The invention further provides methods for the production of the compounds of the invention, which are described below and in the Examples and Preparations section. The skilled man will appreciate that the substances of the invention could be made by methods other than those described herein, by adaptation of the methods described herein and/or adaptation of a plethora of methods known in the art. It is to be understood that the synthetic transformation methods specifically mentioned herein may be carried out in various different sequences to efficiently assemble the desired substances. The skilled chemist will exercise his/her judgement and skill as to the most efficient sequence of reactions for synthesis of a given target substance.

It will also be apparent to those skilled in the art that sensitive functional groups may need to be protected and deprotected during synthesis of a substance of the invention. This may be achieved by conventional techniques, for example, as described in 'Protective Groups in Organic Synthesis' by T W Greene and P G M Wuts, John Wiley and Sons Inc, 1991.

Compounds of formula (I) may be prepared in accordance with the following reaction Scheme I. Unless otherwise specified, the substituents are as defined above with reference to the compounds of formula (I) above.

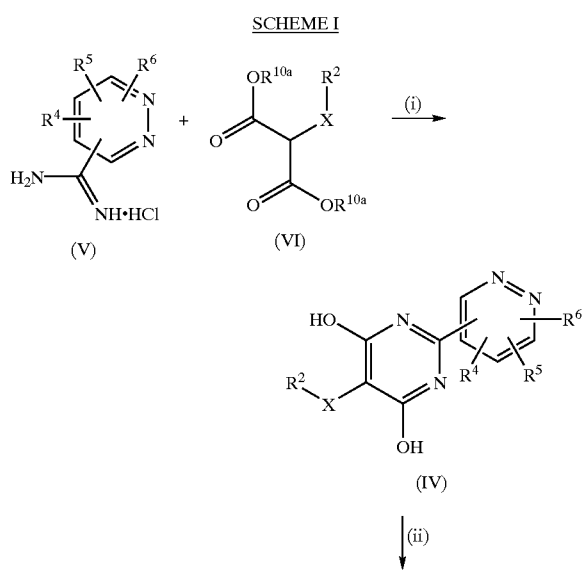

Compounds of formula (IV) may be prepared from compounds of formula (V) and (VI), where $R^{10a}$ is a ($C_1$–$C_6$) alkyl or phenyl group, by process step (i), a condensation reaction. This is typically conducted in the presence of $R^{10a}$ONa in a solvent of the corresponding alcohol $R^{10a}$OH.

Compounds of formula (III) may be prepared by treating compounds of formula (IV) with a chlorinating agent in process step (ii). For example, by treating compounds of formula (IV) with $SOCl_2$ or phosphorus oxychloride in the presence of a base which may be inorganic (e.g., sodium hydrogen carbonate) or organic (e.g., diethylisopropylamine). The reaction is optionally conducted employing an inert solvent (e.g., tetrahydrofuran), optionally cooled or heated. When tetrahydrofuran is used as solvent, the reaction is preferably conducted at a temperature from about 60° C. to about 65° C.

Compounds of formula (II) may be prepared under the conditions of process step (iii) by treating compounds of formula (III) with $R^1SO_2NH_2$ in the presence of a base such as potassium carbonate. The reaction requires heat and should be conducted in a suitable solvent such as DMSO.

$R^1SO_2NH_2$ may be prepared by treating the corresponding bromide with $Na_2SO_3$ in water/DME, followed by $PCl_5$ in toluene or $POCl_3$, followed by reaction with aqueous $NH_3$ in ethanol. $R^1Br$ is commercially available or may be prepared by methods well known to one skilled in the art.

Compounds of formula (I) may be prepared under the conditions of process step (iv) by reacting compounds of formula (II) with $R^3YH$ in the presence of a suitable base (eg NaH) and solvent. $R^3YH$ is used as a solvent, where suitable, with optional use of an inert solvent (e.g., tetrahydrofuran or dimethylformamide) and optional heat.

Compounds of formula (V) may be prepared in accordance with the following reaction Scheme II.

SCHEME II

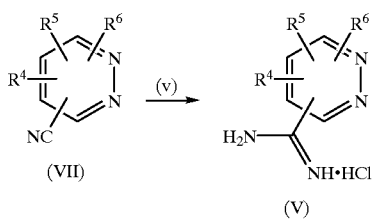

Compounds of formula (V) may be prepared under the conditions of process step (v) by treating a compound of formula (VII) with an alkoxide in a solvent of the corresponding alcohol, such as methoxide in methanol, followed by reaction with $NH_4Cl$. Synthesis of pyridazinecarbonitriles can be found in the literature, such as Dostal et al., *Heterocycles* (1986), 24(3), 793–7.

The introduction and transformation of functional groups on aromatic heterocycles is well described in the literature and the principles can be applied to provide the desired pyridazines by one of ordinary skill in the art. Literature references include Tisler et al., *Adv. Heterocycl. Chem* (1990), 49 385–474 and Heinisch, *Bull. Soc. Chim. Belg.* (1992), 101(7), 579–96.

Compounds of formula (VI) may be prepared in accordance with the following reaction Scheme III.

SCHEME III

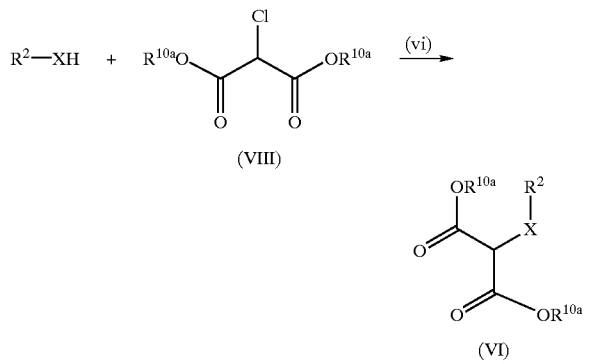

Compounds of formula (VI) may be prepared by reacting a compound of formula (VIII) with $R^2XH$ in the presence of an alkoxide or phenoxide in a solvent of the corresponding alcohol (e.g., NaOMe in MeOH), or in the case of when $R^{10a}$ is phenyl, a suitable inert solvent (e.g., tetrahydrofuran). Compounds of formula (VIII) and $R^2XH$ are commercially available, or may be easily prepared by one skilled in the art. Where X is a direct link, compounds of formula (VI) can be made using literature methods such as those found in U.S. Pat. No. 5,750,766, incorporated herein by reference.

Compounds of formula (IA) where $R^1$, $R^2$, $R^4$, $R^5$, $R^6$ and X are as described above and the $YR^3$ chain is $OCH_2CH_2OH$, with the proviso that $R^4$, $R^5$ and $R^6$ are not $CO_2R^9$ or alkyl chloride or bromide, may be further elaborated to give the corresponding compound of formula (IB) where $YR^3$ is $OCH_2CH_2OC(O)NH$-heteroaryl or $OCH_2CH_2OC(O)NH$-(benzofused heteroaryl). These compounds may be prepared in accordance with the following reaction Scheme IV.

SCHEME IV

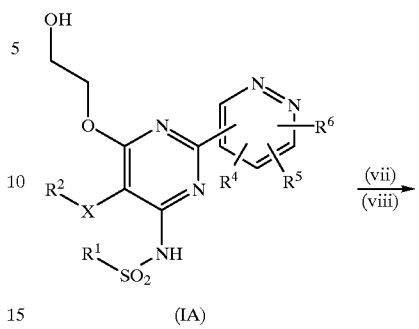

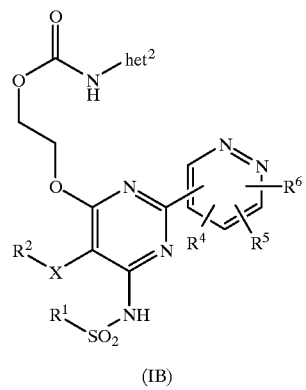

Compounds of formula (IA) are reacted under the conditions of process step (vii) with an agent to activate the alcohol such as phosgene or carbonyldiimidazole. This intermediate is then reacted under the conditions of process step (viii) with $H_2N$-heteroaryl (or $H_2N$-(benzofused heteroaryl)) in the presence of a suitable base such as triethylamine to give (IB).

Compounds of formula (IA) where $R^1$, $R^2$, $R^4$, $R^5$, $R^6$ and X are as described above and the $YR^3$ chain is $OCH_2CH_2OH$ (with the proviso that $R^4$, $R^5$ and $R^6$ are not $CO_2R^9$ or alkyl chloride or bromide) may be further elaborated to give the corresponding compound of formula (IC) where $YR^3$ is $OCH_2CH_2O$-heteroaryl or $OCH_2CH_2O$-(benzofused heteroaryl). These compounds may be prepared in accordance with the following reaction Scheme V.

SCHEME V

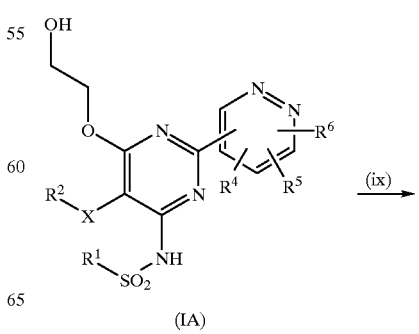

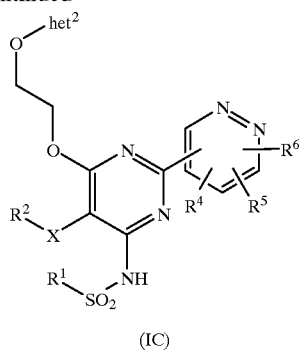

(IC)

Compounds of formula (IA) were treated under the conditions of process step (ix) by reacting compound (IA) with heteroaryl-Z (or (benzofused heteroaryl)-Z), where Z is a suitable leaving group such as halo or $SO_2Me$, in the presence of a suitable base such as sodium hydride.

Compounds of formula (ID) where $R^1$, $R^2$, $R^3$, $R^4$, $R^5$, Y and X are as described above and $R^6$ is $CO_2R^9$ (with the proviso that there are no other ester, ketone or hydroxy moieties within the molecule) may be further elaborated to give the corresponding compound of formula (IF) where $R^6$ is $CH_2F$ or (IG) where $R^6$ is $CF_2H$. These compounds may be prepared in accordance with the following reaction Scheme VI.

SCHEME VI

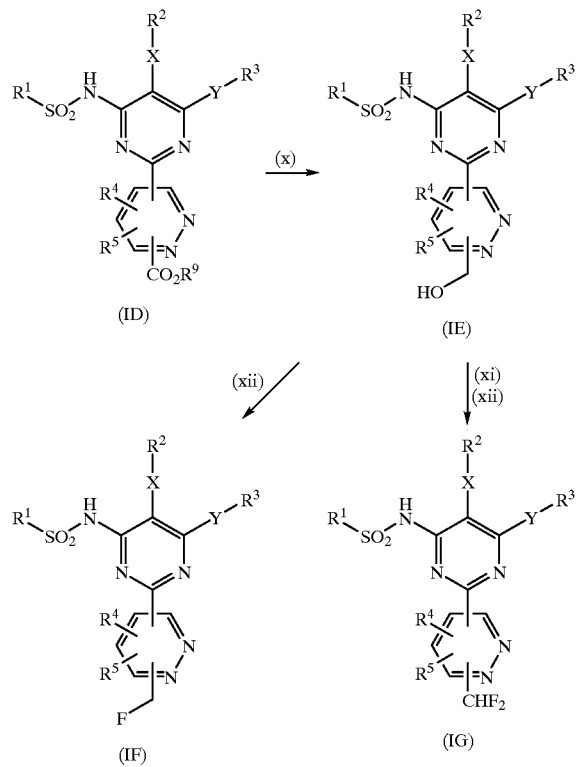

Compounds of formula (ID) are treated under the conditions of process step (x) via a reduction, with a suitable reagent such as DIBAL or $LiAlH_4$ to give the corresponding alcohol (IE). The alcohol may be oxidized to an aldehyde via process step (xi) using a suitable oxidant such as pyridinium dichromate or $MnO_2$, followed by fluorination in process step (xii) by reaction with a suitable fluorinating agent such as diethylaminosulfur trifluoride (DAST) to give compound (IG). Compounds of formula (IE) may also be converted to compounds of formula (IF) under the conditions of process step (xii) described above.

The compounds of the invention may be separated and purified by conventional methods.

The compounds of the present invention are useful because they block ET receptors and are thus useful in the treatment or prevention of any diseases for which such a blockade is beneficial. More particularly, they are useful in the treatment and prevention of restenosis, acute/chronic renal failure, hypertension including pulmonary and systemic hypertension; benign prostatic hypertrophy, male erectile dysfunction, prostate cancer, metastatic bone cancer, congestive heart failure, stroke, subarachnoid haemorrhage, angina, atherosclerosis, cerebral and cardiac ischemia, prevention of ischemia/reperfusion injury (e.g. allografts), cyclosporin induced nephrotoxicity, glaucoma, radiocontrast nephropathy, diabetic neuropathy, allergy, restoration of organ perfusion in haemorrhagic shock, lipoprotein lipase related disorders, chronic obstructive pulmonary disease and hyaline membrane disease in newborn. The treatment of congestive heart failure, restenosis, renal failure and systemic and pulmonary hypertension are of particular interest. The substances of the invention may be administered alone or as part of a combination therapy.

The invention also provides a compound of formula (I) or a pharmaceutically acceptable derivative thereof for use as a medicament.

The invention also provides for the use of a compound of formula (I) or pharmaceutically acceptable derivative thereof as defined above, in the manufacture of a medicament for the treatment of conditions mediated by endothelin, particularly $ET_A$, more particularly restenosis, acute/chronic renal failure, pulmonary hypertension, systemic hypertension; benign prostatic hyperplasia, male erectile dysfunction, prostate cancer, metastatic bone cancer, congestive heart failure, stroke, subarachnoid haemorrhage, angina, atherosclerosis, cerebral and cardiac ischemia, prevention of ischaemia/reperfusion injury (e.g. allografts), cyclosporin induced nephrotoxicity, glaucoma, radiocontrast nephropathy, diabetic neuropathy, allergy, restoration of organ perfusion in haemorrhagic shock, lipoprotein lipase related disorders, chronic obstructive pulmonary disease and hyaline membrane disease in newborn.

The invention also provides a method of treating conditions mediated by endothelin, particularly $ET_A$, which comprises administering to a patient in need of such treatment a therapeutically effective amount of a compound of formula (I) or a pharmaceutically acceptable derivative thereof.

Reference to treatment herein includes prevention of undesirable conditions as well as alleviation or cure of said conditions.

The biological activity of the substances of the invention may be demonstrated as follows:

Human Binding assay

Competition between test substances and [125I]-ET-1 binding to human endothelin receptors is determined as follows.

Binding to $ET_A$ receptors

25 µl of a 30 pM solution of [125I]Tyr[13] ET-1 (specific activity 2,200 Ci/mM) is mixed with 25 µl samples of test substance (final concentrations in the range 0.1 nM–50,000 nM). 200 µl of a solution containing cloned human $ET_A$ receptor (0.75 pmoles receptor protein/ml), 50 mM Tris, 0.5 mM $CaCl_2$, 0.1% human serum albumen, 0.1% bacitracin, 0.05% Tween 20, pH 7.4 is added. The solution is mixed at 37° C. for 2 hours. After the incubation, the unbound ligand is separated from receptor bound ligand by filtration with a Brandel cell harvester, followed by three washes of buffer. Filter papers are counted for radioactivity, and the $IC_{50}$ (the concentration of test compound at which 50% of the radio-labelled compound is unbound) determined for the concentration range tested.

Binding to $ET_B$ receptors

25 µl of a 30 pM solution of $[^{125}I]Tyr^{13}$ ET-1 (specific activity 2,200 Ci/mM) is mixed with 25 µl samples of test substance (final concentration 0.1 nM–50,000 nM). 200 µl of a solution containing cloned human $ET_B$ receptor (0.25 pmoles receptor protein/ml), 50 mM Tris, 0.5 mM $CaCl_2$, 0.1% human serum albumen, 0.1% bacitracin, 0.05% Tween 20, pH 7.4 is added. The solution is mixed at 37° C. for 2 hours. After the incubation, the unbound ligand is separated from receptor bound ligand by filtration with a Brandel cell harvester, followed by three washes of buffer. Filter papers are counted for radio-activity, and the $IC_{50}$ (the concentration of test compound at which 50% of the radio-labelled compound is unbound) determined for the concentration range tested.

The compounds of the present invention were tested and found to have good affinity for endothelin receptors and to be selective for $ET_A$ over $ET_B$.

Dog Binding assay

Competition between test substances and ligands binding to canine endothelin receptors is determined as follows:

Dog $ET_A$ Binding Assay

50 µl of a 500 pM solution of $^{125}$I-PD-1 51242 (Specific activity 2,000 Ci/mM) is mixed with 50 µl samples of test substances (final concentrations in the range from 0.01–10,000 nM). 100 µg of purified dog kidney homogenate is added in 150 µl of the following buffer: 50 mM Tris, 10 mM $MgCl_2$ and 0.05% Bovine Serum Albumen at pH 7.4. The solution is incubated at room temperature for 2 hours. After the incubation, the unbound ligand is separated from receptor bound ligand by filtration with a Brandel cell harvester, followed by 5 washes with buffer (Tris 50 mM, $MgCl_2$ 10 mM). Filter papers are counted for radioactivity and the $K_i$ (an $IC_{50}$ corrected for the dissociation constant and concentration of the ligand added) is determined for the concentration range tested.

Dog $ET_B$ Binding Assay

50 µl of a 100 pM solution of $^{125}$I-IRL-1620 (Specific activity 2,200 Ci/mM) is mixed with 50 µl samples of test substances (final concentrations in the range from 0.01–10,000 nM). 50 µg of purified Dog cerebellum homogenate is added in 150 µl of the following buffer; 50 mM Tris, 10 mM $MgCl_2$ and 0.05% Bovine Serum Albumen at pH 7.4. The solution is incubated at 30° C. for 90 minutes. After the incubation, the unbound ligand is separated from receptor bound ligand by filtration with a Brandel cell harvester, followed by 5 washes with buffer (Tris 50 mM, $MgCl_2$ 10 mM). Filter papers are counted for radioactivity and the $K_i$ (an $IC_{50}$ corrected for the dissociation constant and concentration of the ligand added) is determined for the concentration range tested.

The compounds of the present invention were investigated using the above assay and demonstrated strong $ET_A$ affinity and a marked selectivity for the $ET_A$ over the $ET_B$ receptor. Of the compounds disclosed, the compound of example 5 displays affinity and selectivity for the dog $ET_A$ receptor (Ki 2 nM) vs dog $ET_B$ (Ki 132 nM).

According to a further aspect of the invention, there are provided pharmaceutical formulations comprising a compound of the present invention, as defined above, and a pharmaceutically-acceptable adjuvant, diluent or carrier.

The compounds of the present invention can be administered alone but will generally be administered in admixture with a pharmaceutical carrier selected with regard to the intended route of administration and standard pharmaceutical or veterinary practice. For example they can be administered orally in the form of tablets containing such excipients as starch or lactose or in capsules or ovules either alone or in admixture with excipients or in the form of elixirs, solutions or suspensions containing the substance in a liquid carrier, for example a vegetable oil, glycerine or water with a flavoring or coloring agent. They can be injected parenterally, for example intravenously, intramuscularly or subcutaneously. For parental administration, they are best used as sterile aqueous solutions which may contain other substances, for example, enough glucose or salts to make the solution isotonic with blood. For parenteral administration the substance may also be administered as a solution or suspension in a suitable oil, for example polyethylene glycol, lecithin or sesame oil.

Compounds of the present invention may also be administered through inhalation of a solution, suspension or emulsion that may be administered as a dry powder or in the form of an aerosol using a conventional propellant such as dichlorodifluoromethane.

For oral or parenteral administration to human patients the daily dosage levels of substances of the invention will be from about 0.01 to about 30 mg/kg (in single or divided doses) and preferably will be in the range from about 0.01 to about 5 mg/kg. Thus tablets will contain about 1 mg to about 0.4 g of substance for administration singly or two or more at a time, as appropriate. The above dosages are, of course only exemplary of the average case and there may be instances where higher or lower doses are merited, and such are within the scope of the invention.

General Example

A formulation of the tablet could typically contain between about 0.01 mg and about 500 mg of active compound whilst tablet fill weights may range from about 50 mg to about 1000 mg. An example of a formulation for a 10 mg tablet is illustrated below:

| Ingredient | % w/w |
| --- | --- |
| Free acid, Free base or Salt form of active compound | 10.000 |
| Lactose | 64.125 |
| Starch | 21.375 |
| Croscarmellose sodium | 3.000 |
| Magnesium Stearate | 1.500 |

The tablets are manufactured by a standard process. For example, direct compression or a wet or dry granulation process. The tablet cores may be coated with appropriate overcoats.

Alternatively the substances of the invention can be administered in the form of a suppository or pessary, or they may be applied topically in the form of a lotion, solution, cream, ointment or dusting powder or in the form of a medicated plaster, patch or membrane. For example they may be incorporated in a cream containing an aqueous emulsion of polyethylene glycols or liquid paraffin. The compounds may also be administered intranasally.

For veterinary use although it is possible to administer a substance of the invention directly without any formulation, the substances are preferably employed in the form of a pharmaceutical or veterinary formulation comprising a pharmaceutically or veterinarily acceptable carrier, diluent or excipient and a substance of the invention. Such compositions will contain from 0.1 percent by weight to 90.0 percent by weight of the active ingredient.

The methods by which the compounds may be administered include oral administration by capsule, bolus, tablet or drench, topical administration as an ointment, a pour-on, spot-on, dip, spray, mousse, shampoo or powder formulation or, alternatively, they can be administered by injection (e.g. subcutaneously, intramuscularly or intravenously), or as an implant.

Such formulations are prepared in a conventional manner in accordance with standard veterinary practice. Thus capsules, boluses or tablets may be prepared by mixing the active ingredient with a suitable finely divided diluent or carrier additionally containing a disintegrating agent and/or binder such as starch, lactose, talc or magnesium stearate, etc. Oral drenches are prepared by dissolving or suspending the active ingredient in a suitable medium. Pour-on or spot-on formulations may be prepared by dissolving the active ingredient in an acceptable liquid carrier vehicle such as butyl digol, liquid paraffin or a non-volatile ester, optionally with the addition of a volatile component such as propan-2-ol.

Alternatively, pour-on, spot-on or spray formulations can be prepared by encapsulation, to leave a residue of active agent on the surface of the animal. Injectable formulations may be prepared in the form of a sterile solution which may contain other substances, for example enough salts or glucose to make the solution isotonic with blood. Acceptable liquid carriers include vegetable oils such as sesame oil, glycerides such as triacetin, esters such as benzyl benzoate, isopropyl myristrate and fatty acid derivatives of propylene glycol, as well as organic solvents such as pyrrolidin-2-one and glycerol formal. The formulations are prepared by dissolving or suspending the active ingredient in the liquid carrier such that the final formulation contains from 0.1 to 10% by weight of the active ingredient.

These formulations will vary with regard to the weight of active substance contained therein, depending on the species of animal to be treated, the severity and type of infection and the body weight of the animal. For parenteral, topical and oral administration, typical dose ranges of the active ingredient are from about 0.01 to about 100 mg per kg of body weight of the animal. Preferably, the range is from about 0.1 to about 10 mg per kg.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

As an alternative for veterinary use the substances may be administered with animal feedstuff and for this purpose a concentrated feed additive or premix may be prepared for mixing with the normal animal feed.

The compounds of the formula (I) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubilizer. Alpha-, beta-and gamma-cyclodextrins are most commonly used and suitable examples are described in PCT publications WO-A-91/11172, WO-A-94/02518 and WO-A-98/551 48.

EXAMPLES

High performance liquid chromatography (HPLC) retention times and UV spectra were recorded using a Hewlett-Packard 1090 LUSI diode-array spectrophotometer (method A). All NMR spectra were measured in CDCl$_3$ or MeOD by an Inova 300 MHz or 400 MHz spectrometer unless otherwise indicated and peak positions are expressed in parts per million (ppm) downfield from tetramethylsilane. The peak shapes are denoted as follows: s, singlet; d, doublet; t, triplet; q, quartet; m, multiplet; br broad. High resolution MS data was acquired on an AutoSpecQ with electrospray ionisation (ESI) or thermospray ionization (TSPI) using a PEG reference (or on a Brüker Apex II FTMS with ESI where indicated). All calculated MS values for compounds including Cl are based on the $^{35}$Cl isomer. All IR spectra were recorded using a Perkin Elmer Paragon 1000 FT-IR.

Preparation 1
3-Pyridazinecarboximidamide hydrochloride

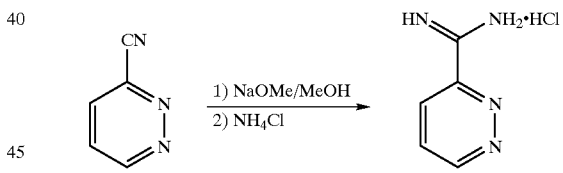

Sodium methoxide (25% w/v in methanol, 0.3 ml, 1.3 mmol) was added in one portion to a stirred solution of 3-cyanopyridazine (2.4 g g, 22.9 mmol) (Ref. *Heterocycles*, 1986, 24(3), 793) in methanol (10 ml). The resulting mixture was stirred at room temperature for 16 hours. Ammonium chloride (2.45 g, 45.8 mmol) was added to the reaction mixture, which was then stirred for 30 minutes before being ultrasonicated for a further 15 minutes. A fine, yellow precipitate was observed after this time. The solvent was evaporated under vacuum and the residue was suspended in ethanol (150 ml) and heated to reflux for 5 minutes. The hot mixture was filtered (gravity) to remove unreacted ammonium chloride and sodium chloride and was then cooled to room temperature. A pale yellow, crystalline solid formed upon cooling and this was isolated by suction filtration to give the title compound (2.03 g), m.p. 234°–241° C.

$^1$H-NMR (300 MHz, DMSO-D$_6$): □8.08 (dd, 1H), 8.54 (d, 1H), 9.53 (d, 1H) ppm.

IR (KBr disk): λ 1404, 1692, 3040, 3143, 3431, 3469 cm$^{-1}$.

Preparation 2

5-(2-Methoxyphenoxy)-2-(3-pyridazinyl)-4,6-pyrimidinediol

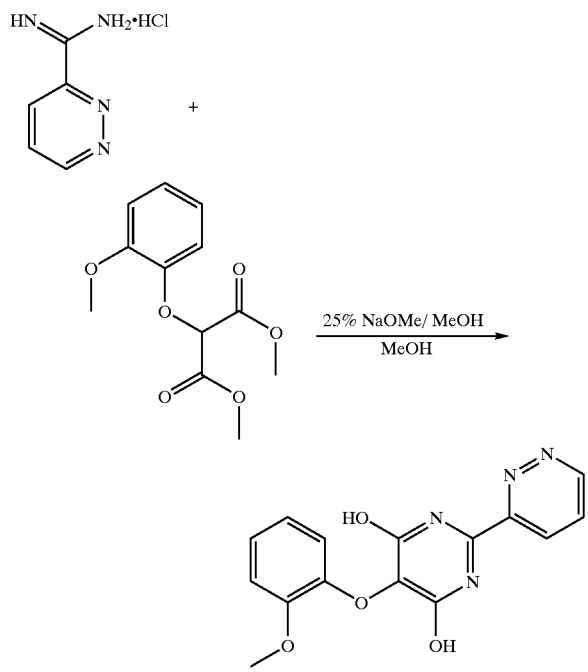

Dimethyl 2-(2-methoxyphenoxy)malonate (3.05 g, 12.6 mmol) (Ref. Canadian Patent Application No. CA2071193A, 1992) in methanol (15 ml) was added over 5 minutes to a stirred, 25% w/v solution of sodium methoxide in methanol (8.58 ml, 37.8 mmol of sodium methoxide) at room temperature. The resulting mixture was stirred for 10 minutes and then a solution of 3-pyridazinecarboximidamide hydrochloride (2.0 g, 12.6 mmol) in methanol (15 ml) was added dropwise over 5 minutes and the resulting mixture was stirred at room temperature overnight. The reaction mixture was concentrated under vacuum and then diluted with water (100 ml). The aqueous solution was acidified to pH 4 with sulfuric acid (20%), resulting in the formation of the title compound as a purple solid, which was isolated by filtration (1.4 g).

$^1$H-NMR (300 MHz, DMSO-d$_6$): □3.83 (s, 3H), 6.68 (d, 1H), 6.78 (t, 1H), 6.93 (t,1H), 7.03 (d,1H), 7.94 (dd,1H), 8.34 (d,1H), 9.43 (d,1H) ppm. HRMS (+ve ion) found: m/z 313.0929 (MH$^+$). C$_{15}$H$_{12}$N$_4$O$_4$+H requires m/z 313.0932

Preparation 3

3-[4,6-Dichloro-5-(2-methoxyphenoxy)-2-pyrimidinyl]pyridazine

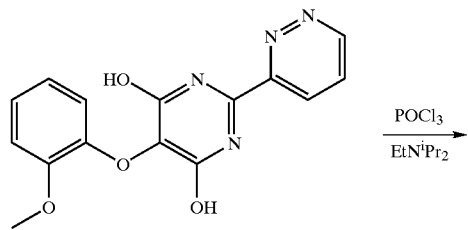

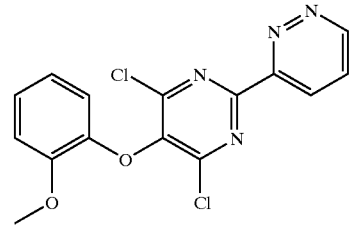

A solution of 5-(2-methoxyphenoxy)-2-(3-pyridazinyl)-4,6-pyrimidinediol (1.4 g, 4.5 mmol) and diisopropylethylamine (1.28 g, 9.9 mmol) in phosphorus oxychloride (7 ml) was stirred for 1 hour at room temperature under a nitrogen atmosphere and then heated under reflux for 1 hour before being cooled to room temperature and stirred for 72 hr. The reaction mixture was heated under reflux for a further 7 hours and then again cooled to room temperature and stirred for a further 16 hours.

The reaction mixture was added slowly to a stirred aqueous solution of hydrochloric acid (0.1 M, 200 ml) at 50° C. over 20 minutes. A precipitate formed and was isolated by filtration. The isolated crude product was purified by chromatography on a Biotage® Flash 40(s) silica cartridge (40 g) using 70% ethyl acetate/ heptane as eluant to give the title compound as a light brown solid (1.1 g), R$_f$ 0.59 (ethyl acetate).

$^1$H-NMR (300 MHz, CDCl$_3$): □3.86 (s, 3H), 6.79 (d, 1H), 6.91 (t, 1H), 7.02 (d, 1H), 7.13 (t, 1H), 7.72 (dd, 1H), 8.58 (dd, 1H), 9.36 (d, 1H) ppm. HRMS (+ve ion) found: m/z 349.0247 (MH$^+$). C$_{15}$H$_{10}$$^{35}$Cl$_2$N$_4$O$_2$+H requires m/z 349.0253.

Preparation 4

2-(4-Fluorophenyl)ethanesulfonic acid sodium salt

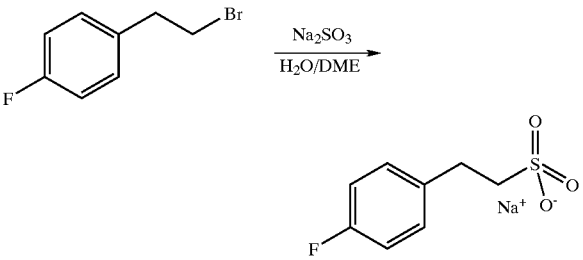

A mixture of 2-(4-fluorophenyl)ethyl bromide (1.8 g, 8.9 mmol) (Ref. *Chim. Ther.*, 1969, 4(3),185) and sodium sulfite (2.24 g, 8.9 mmol) in water (5 ml) and dimethoxyethane (5 ml) was heated under reflux for 21 hours. The mixture was then left for 72 hours at room temperature. The mixture was concentrated under vacuum to leave the title compound as a crytalline mixture with sodium bromide (2.87 g).

$^1$H-NMR (300 MHz, D$_2$O): □2.96 (m, 2H), 3.09 (m, 2H), 7.03 (dd, 2H), 7.25 (dd, 2H) ppm. LRMS (-ve ion) found: m/z 203 (M$^-$). C$_8$H$_8$FO$_2$S requires 203.

The following examples were also prepared by a similar method to that described for preparation 4.

| Prep. No. | R | Reference/source (starting material) | Analytical data |
|---|---|---|---|
| 5 | 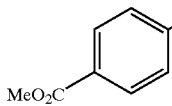 MeO₂C— | J. Med. Chem., 1997, 40(16), 2502 | ¹H-NMR(300 MHz, D₂O): □3.08(t, 2H), 3.15(t, 2H), 3.86 (s, 3H), 7.37(d, 2H), 7.91(d, 2H) ppm. MS - no ionisation |
| 6 | 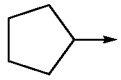 | J. Med. Chem., 1981, 24(4), 404 | ¹H-NMR(300 MHz, D₂O): □ 0.8–1.65(m, 10H), 1.75(m, 1H), 2.80(t, 2H) ppm. |

Preparation 7
2-(4-Fluorophenyl)ethanesulfonyl chloride

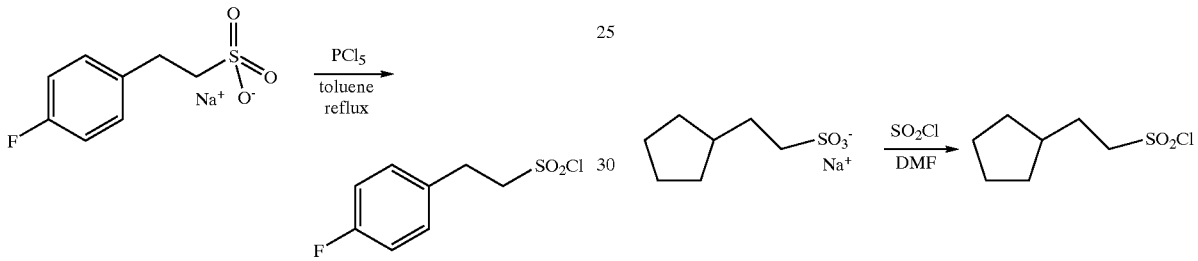

Phosphorus pentachloride (5.6 g, 27 mmol) was added portionwise over 10 minutes to a stirred suspension of 2-(4-fluorophenyl)ethanesulfonic acid sodium salt (9 mmol, contaminated with sodium bromide, total weight 2.87 g) in dry toluene (15 ml) at room temperature. The reaction mixture was heated under reflux for 90 minutes and was then stirred at room temperature overnight. The reaction mixture was diluted with water (20 ml) and the organic phase was separated. The aqueous phase was extracted with dichloromethane (20 ml) and the organic extracts were combined, dried over magnesium sulfate and concentrated under vacuum to give the title compound as an oil, (0.7 g) $R_f$ 0.92 (dichloromethane).

¹H-NMR (300 MHz, CDCl₃): □3.33 (m, 2H), 3.89 (m, 2H), 7.07 (dd, 2H), 7.23 (dd, 2H) ppm.

IR (NaCl disk): λ 1599, 1509, 1450, 1354 cm⁻¹

The following compounds were prepared by similar methodology.

$RCH_2CH_2SO_2Cl$

Preparation 9
2-(Cyclopentyl)ethylsulfonyl chloride

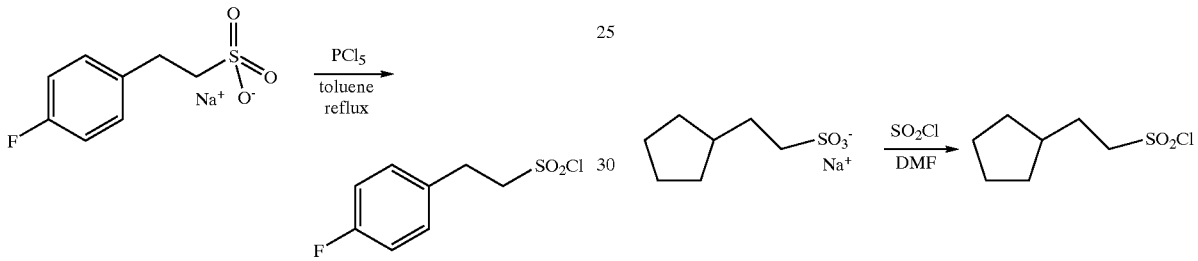

Dimethylformamide (5 drops) was added over 1 minute to a stirred solution of 2-(cyclopentyl)ethylsulfonic acid sodium salt (1 5.5 g, 87.5 mmol) in thionyl chloride (60 ml) under a nitrogen atmosphere. The reaction mixture was stirred under reflux for 5 hours and was then cooled to room temperature and concentrated under vacuum. The residue was suspended in toluene (100 ml) and then concentrated under vacuum. The residue was dissolved in a mixture of ethyl acetate (150 ml) and water (150 ml) and the organic phase was separated. The aqueous phase was extracted with ethyl acetate (100 ml) and the combined organic extracts were washed with brine (3×100 ml), dried (magnesium sulfate) and evaporated to give the title compound as a brown oil (14.1 g), $R_f$ 0.5 (pentane/ethyl acetate 95:5).

¹H-NMR (300 MHz, CDCl₃): □1.15 (m, 2H), 1.50–1.72 (m, 4H), 1.84 (m, 2H), 1.91 (m, 1H), 2.03 (m, 2H), 3.66 (m, 2H) ppm.

| Preparation No. | R | Yield | Analytical data |
|---|---|---|---|
| 8 | 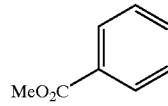 MeO₂C— | 1.5 g | ¹H-NMR(300 MHz, CDCl₃): □3.24(t, 2H), 3.58(t, 2H), 3.92(s, 3H), 7.28(d, 2H), 8.00(d, 2H) ppm. MS m/z 260(MNH₄⁺) IR λ 2952, 1721, 1611, 1435, 1280, 1180 cm⁻¹ |

Preparation 10
2-(4-Fluorophenyl)ethanesulfonamide

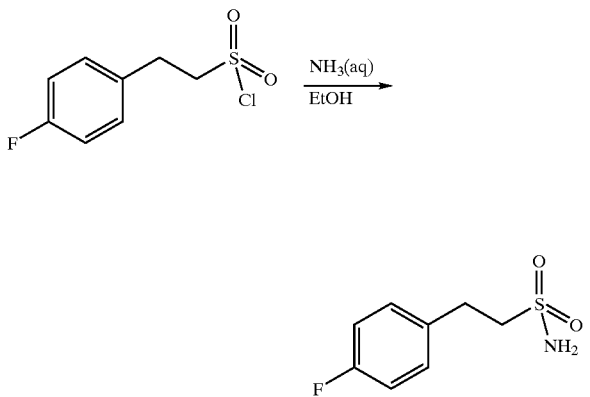

A mixture of 2-(4-flourophenyl)ethanesulfonyl chloride (0.7 g, 3.3 mmol) and concentrated aqueous ammonia (0.88 specific gravity, 10 ml) in ethanol (5 ml) was stirred at room temperature overnight. The reaction mixture was diluted with water (10 ml), acidified to pH 4 with citric acid (1.0 M) and then extracted with dichloromethane. The organic extracts were dried by filtering through an organic-only, permeable membrane and then concentrated under vacuum. The residue was purified by chromatography on a Biotage® Flash 40 (s) column (40 g silica) using 10–20% ethyl acetate/dichloromethane as eluant to give the title compound as an off white solid, (0.66 g).

$^1$H-NMR (300 MHz, CDCl$_3$): δ2.98 (m, 2H), 3.23 (m, 2H), 7.11 (dd, 2H), 7.29 (dd, 2H) ppm. IR (KBr disk): λ 3357, 3254, 3068, 2962, 1907, 1598, 1509, 1321, 1161 cm$^{-1}$ LRMS (−ve ion) found: m/z 202 (M−H). C$_8$H$_{10}$FNO$_2$S—H requires m/z 202

The following compounds were prepared by similar methodology.

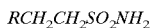

Preparation 13
2-(Cyclopentyl)ethanesulfonamide

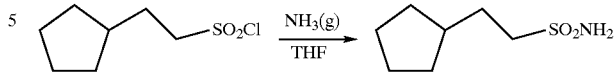

A solution of 2-(cyclopentyl)ethanesulfonyl chloride (14.1 g, 71.4 mmol) in dry tetrahydrofuran (40 ml) was saturated with gaseous ammonia at 0° C. The resulting solution was stirred at room temperature under nitrogen for 2 hours and then concentrated under vacuum. The residue was dissolved in ethyl acetate (50 ml) and water (50 ml) and the aqueous phase was then acidified to pH 2 with 2.0 M aqueous hydrochloric acid. The organic phase was separated and then washed with water (2×30 ml), dried (sodium sulfate) and concentrated under vacuum. Purification of the residue by chromatography on silica (500 g) using 65/35 pentane/ethyl acetate as eluant gave the title compound as an off-white solid (6.48 g), R$_f$ 0.7 (pentane/ethyl acetate 1:1).

$^1$H-NMR (300 MHz, CDCl$_3$) δ1.12 (m, 2H), 1.48–1.68 (m, 4H), 1.73–1.94 (5H, m), 3.10 (m, 2H), 4.55 (broad s, 2H) ppm LRMS (+ve ion) found: m/z 195 (MNH$_4^+$). C$_7$H$_{15}$NO$_2$S+ NH$_4^+$ requires m/z 195

Preparation 14
N-[6-Chloro-5-(2-methoxyphenoxy)-2-(3-pyridazinyl)-4-pyrimidinyl]-2-(1-naphthyl) ethanesulfonamide

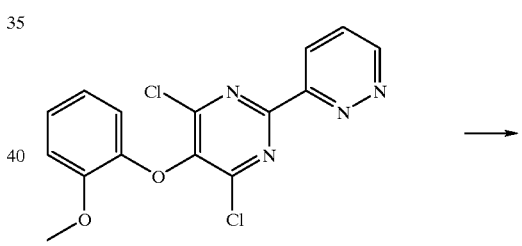

| Preparation No. | R | MS | Analytical data |
|---|---|---|---|
| 11 | 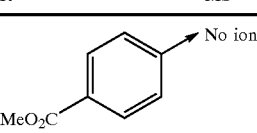 MeO$_2$C- | No ion | $^1$H-NMR(300 MHz, CDCl$_3$): δ3.24(t, 2H), 3.58(t, 2H), 3.92(s, 3H), 7.28(d, 2H), 8.00(d, 2H) ppm. IR λ 3354, 3267, 3067, 3009, 2956, 1718, 1611, 1554, 1428, 1310, 1282, 1160 cm$^{-1}$ m.p. 129–130.5° C. |
| 12$^a$ | 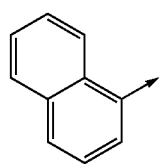 | 234(M − H), 253(MNH$_4$+) | $^1$H-NMR(300 MHz, DMSO-D$_6$): δ3.32(m, 2H), 3.47(m, 2H), 6.97(broad s, 2H), 7.46(m, 2H), 7.56(m, 2H), 7.83(m, 1H), 7.94(d, 1H), 8.06(d, 1H) ppm. IR λ 3335, 3261, 3051, 1598, 1549, 1317, 1167 cm$^{-1}$ m.p. 176–178° C. |

$^a$2-(1-naphthyl)ethanesulfonylchloride was purchased from TCI Tokyo Kasei Kogyo Co., Ltd.

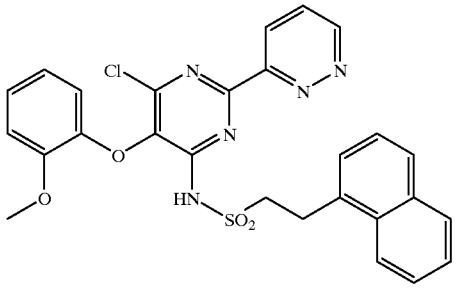

To a solution of 3-[4,6-dichloro-5-(2-methoxyphenoxy)-2-pyrimidinyl] pyridazine, (0.06 g, 0.7 mmol) in dimethylsulfoxide (4 ml) was added potassium carbonate (0.13 g, 0.94 mmol) immediately followed by 2-(1-naphthyl) ethanesulfonamide (0.044 g, 0.18 mmol). The mixture was stirred vigorously for 72 hours at 90° C. and then quenched with hydrochloric acid solution (2 M, 4 ml). Ice-cold water (5 ml) was added and a white precipitate was observed. The resultant mixture was partitioned between water (10 ml) and dichloromethane (3×10 ml). The combined organic extracts were washed with water (3×10 ml), dried (magnesium sulfate) and concentrated under vacuum, yielding a yellow oil. Trituration with 1 ml of ice cold water, followed by filtration gave the title compound as a white solid (0.088 g), m.p. 191.5° C.

$^1$H-NMR (300 MHz, CDCl$_3$) δ 3.6 (t, 2H), 3.98 (s, 3H), 4.12 (t, 2H), 6.91 (t, 1H), 7.02 (d, 1H), 7.1–7.3 (m, 7H), 7.7(d, 1H), 7.8 (t, 1H), 8.3 (d, 1H), 9.3 (d, 1H) ppm.

IR (NaCl disk) λ 2996.5, 2913.0, 1436.9, 1406.2, 1057.2 cm$^{-1}$.

LRMS (+ve ion) found: m/z 549 (MH$^+$). C$_{27}$H$_{22}$$^{35}$ClN$_5$O$_4$S+H requires m/z 549.

The compounds of the following tabulated preparations of the general formula:

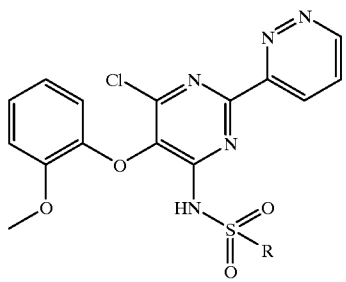

were prepared by a similar method to that of Preparation 14 using the appropriate sulfonamide starting materials and the dichloropyrimidine of Preparation 3.

| No. | R | Mp °C. | LRMS m/z = | Analytical data |
|---|---|---|---|---|
| 15 | 4-fluorophenylethyl | 142.8 | 516.4 [MH]$^+$ | $^1$H-NMR(300 MHz, CDCl$_3$): □3.18(t, 2H), 3.95(s, 3H), 4.10(t, 2H), 4.91(bs, 1H), 6.9–7.2(m, 8H), 7.62(m, 1H), 8.4(d, 1H), 9.3(d, 1H) ppm. IR λ 2996.9, 2913.3, 1437.0, 1406.5, 1057.1 and 935.7 (cm$^{-1}$) |
| 16 | cyclopentylethyl | 121.1 | 491.2 [MH]$^+$ | $^1$H-NMR(300 MHz, CDCl$_3$): □(bm, 2H), 1.5(bm, 3H), 1.8(bm, 4H), 2.3(t, 2H), 3.7(t, 2H), 3.95(s, 3H), 6.8–7.2(m, 4H), 7.7(m, 1H), 8.5(m, 1H), 9.3(d, 1H) ppm IR λ 2996.2, 2913.3, 1562.3, 1540.1, 1437.1, 1406.1, 1057.3 (cm$^{-1}$) |
| 17 | 4-(methoxycarbonyl)phenylethyl | 117.8 | 556.4 [MH]$^+$ | $^1$H-NMR(300 MHz, CDCl$_3$): □3.25(t, 2H), 3.9(s, 3H), 3.95(s, 3H), 4.2(t, 2H), 6.9–7.2(m, 4H), 7.3(d, 2H), 7.7(bs, 1H), 7.9(d, 2H), 8.4(d, 1H), 8.7(d, 1H), 9.3(bs, 1H) ppm. IR λ 2996.1, 2913.0, 1435.2, 1406.5, 1057.0 cm$^{-1}$. |
| 18 | phenylethyl | 168.9 | 498.0 [MH]$^+$ | $^1$H-NMR(300 MHz, CDCl$_3$): □3.2(t, 2H), 3.95(s, 3H), 4.1(t, 2H), 6.9(t, 1H), 7.05(d, 1H), 7.1–7.3(m, 7H), 7.6(dd, 1H), 8.4(d, 2H), 8.7(bs, 1H), 9.3(d, 1H) ppm. |

Example 1
N-[6-Methoxy-5-(2-methoxyphenoxy)-2-(3-pyridazinyl)-4-pyrimidinyl]-2-(1-naphthyl) ethanesulfonamide

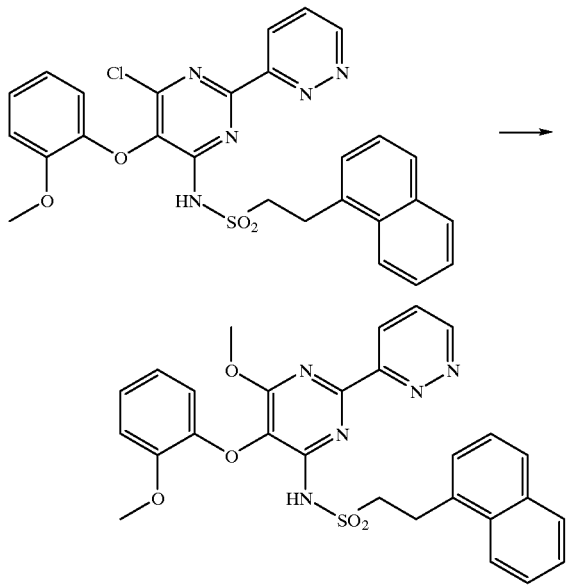

To a solution of N-[6-chloro-5-(2-methoxyphenoxy)-2-(3-pyridazinyl)-4-pyrimidinyl]-2-(1-naphthyl) ethanesulfonamide (0.088 g, 0.17 mmol) (Preparation 14) in methanol (5 ml) was added sodium methoxide (25% w/v in methanol, 1.0 ml). The mixture was stirred vigorously for 72 hours at 60° C. and then quenched with aqueous hydrochloric acid (2 M, 1 ml). Ice-cold water (2 ml) was added and a white precipitate formed. The resultant mixture was partitioned between water (5 ml) and dichloromethane (3×10 ml). The combined organic extracts were washed with water (3×10 ml), dried (magnesium sulfate) and concentrated under vacuum to give the title compound as a yellow solid (95% pure by HPLC). (0.065 g).

$^1$H-NMR (300 MHz, CDCl$_3$) δ 3.55 (t, 2H), 3.9 (s, 3H), 4.05 (t, 2H), 4.12 (s, 3H), 6.85 (t, 1H), 6.9 (d, 1H), 7.1 (m, 2H), 7.2 (m, 1H), 7.3 (m, 7.4 (m, 1H), 7.65 (m, 1H), 7.75 (d, 1H), 7.85 (d, 1H), 8.25 (d, 1H), 9.2 (d, 1H) ppm.

LRMS (−ve ion) found: m/z 542 (M-H). C$_{28}$H$_{25}$N$_5$O$_5$S—H requires m/z 542

IR (NaCl disk)λ 2360.6, 2253.7, 1584.9, 1498.6, 1405.6, 1328.9, 1096.2, 907.1 cm$^{-1}$ The compounds of the following tabulated Examples of the general formula:

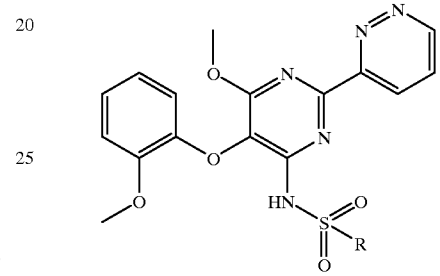

were prepared by a similar method to that of Example 1 using the appropriate 6-chloropyrimidine of Preparations 15–18.

| No. | R | LRMS m/z = | Analytical data |
|---|---|---|---|
| 2 | 4-fluorophenethyl | 512 [MH]$^+$ | $^1$H-NMR(300 MHz, CDCl$_3$): □3.1(t, 2H), 3.9(s, 3H), 4.05(t, 2H), 4.15(s, 3H), 6.85(m, 3H), 6.95(m, 1H), 7.1(m, 4H), 7.6(dd, 1H), 8.35(d, 1H), 8.8(bs, 1H), 9.2(d, 1H) ppm. IR λ 3203.9, 2950.0, 1692.0, 1583.1, 1501.6, 1454.5, 1394.9, 1332.2, 1096.8, 733.1 cm$^{-1}$ |
| 3 | cyclopentylethyl | 486 [MH]$^+$ | $^1$H-NMR(300 MHz, CDCl$_3$): □1.0(m, 2H), 1.4–1.55(m, 4H), 1.65(m, 2H), 1.75(m, 3H), 3.7(t, 2H), 3.9(s, 3H), 4.15(s, 3H), 6.85(t, 3H), 6.95(d, 1H), 7.05(m, 2H), 7.55(m, 1H), 8.4(d, 1H), 8.6(s, 1H), 9.2(d, 1H) ppm. IR λ 2951.9, 2253.8, 1584.7, 1497.8, 1455.2, 1333.2 1253.8, 1096.0, 908.6, 732.3 cm$^{-1}$ |
| 4 | 4-carboxyphenethyl | 536 [M-H]$^+$ | $^1$H-NMR(300 MHz, CDCl$_3$): □3.2(t, 2H), 3.9(s, 3H), 4.05(s, 3H), 4.08(t, 2H), 6.85(t, 1H), 6.95(d, 1H), 7.05(m, 2H), 7.15(d, 2H), 7.6(m, 1H), 7.9(d, 2H), 8.35(d, 1H) ppm. IR λ 3194.9, 2952.0, 2253.9, 1694.0, 1499.0, 1396.0, 1097.0, 1022.2, 908.9, 732.1 cm$^{-1}$ |

| No. | R | LRMS m/z = | Analytical data |
|---|---|---|---|
| 5 | 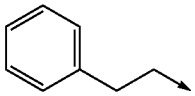 | 494.1496 [MH]+ | ¹H-NMR(300 MHz, CDCl₃): □3.15(t, 2H), 4.0(s, 3H), 4.05(t, 2H), 4.1(s, 3H), 6.9(t, 1H), 7.0(d, 1H), 7.15(m, 7H), 7.7(dd, 1H), 8.5(d, 1H), 8.65(bs, 1H), 9.3(d, 1H) ppm. |

We claim:

1. A compound of formula (I):

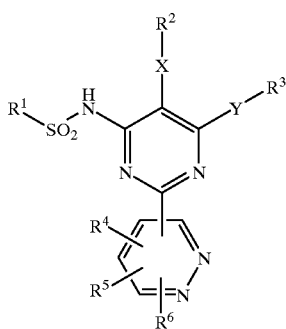

wherein $R^1$ is $(CR^7R^8)_n$—$(C_3$–$C_8)$cycloalkyl, $(CR^7R^8)_n$-heterocycle, $(CR^7R^8)_n$-(benzofused heterocycle), $(CR^7R^8)_n$-aryl, $NR^9R^{10}$, $(CR^7R^8)_n$-heteroaryl, and $(CR^7R^8)_n$-(benzofused heteroaryl), where $R^7$ and $R^8$ are each independently H or $(C_1$–$C_6)$alkyl, $R^9$ and $R^{10}$ are each indepndently H or $(C_1$–$C_6)$alkyl optionally substituted by aryl, heterocycle, benzofused heterocycle, heteroaryl, benzofused heteroaryl, or $(C_3$–$C_8)$cycloalkyl, and n is 2, 3, 4, 5, or 6;

$R^2$ is
(a) phenyl optionally fused with a heterocycle, benzofused heterocycle, heteroaryl, or benzofused heteroaryl,
(b) naphthyl optionally fused with a heterocycle, benzofused heterocycle, heteroaryl, or benzofused heteroaryl, or
(c) heteroaryl or benzofused heteroaryl, where groups (a), (b) and (c) are optionally substituted by $(C_1$–$C_6)$alkyl, $(C_1$–$C_6)$alkoxy, halo, unsubstituted heterocycle, unsubstituted benzofused heterocycle, unsubstituted heteroaryl, unsubstituted benzofused heteroaryl, phenyl, naphthyl, $CO_2R^{11}$, $OC(O)R^{11}$, $CONR^{11}R^{12}$, or $S(O)_pR^{11}$, where p is 0, 1, or 2, and $R^{11}$ and $R^{12}$ are each independently H or $(C_1$–$C_6)$alkyl;

$R^3$ is
(e) $(C_1$–$C_6)$alkyl,
(f) $(C_2$–$C_6)$alkenyl,
(g) $(C_2$–$C_6)$alkynyl, or
(h) $(C_3$–$C_8)$cycloalkyl, where groups (e), (f), (g) and (h) are optionally substituted by $OR^{11}$, halo, $NHC(O)(C_1$–$C_6)$alkyl, O-heterocycle, O-(benzofused heterocycle), O-heteroaryl, O-(benzofused heteroaryl), OC(O)NH-heterocycle, OC(O)NH-(benzofused heterocycle), OC(O)NH-heteroaryl, OC(O)NH-(benzofused heteroaryl), $NH_2$, NHC(O)O-heteroaryl, NHC(O)O-(benzofused heteroaryl), NHC(O)NH-heteroaryl, or NHC(O)NH-(benzofused heteroaryl);

X is O, NH, a direct link, or $S(O)_p$, where p is 0, 1 or 2;
Y is O, NH, or $S(O)_p$, where p is 0, 1 or 2; and
$R^4$, $R^5$ and $R^6$ are each independently selected from the group consisting of H, halo, heterocycle, benzofused heterocycle, heteroaryl, benzofused heteroaryl, aryl, $(C_1$–$C_6)$alkoxy, $(C_1$–$C_6)$alkyl optionally substituted by halo, $OR^9$ or $NH_2$, and $S(O)_pR^9$, where p is 0, 1 or 2;

a pharmaceutically acceptable salt thereof, a prodrug of said compound or said salt, a solvate of said compound, said salt or said prodrug, or a polymorph of said compound, said salt, said prodrug, or said solvate.

2. The compound of claim 1 wherein the pyrimidine ring is attached at the 3 or 4 position of the pyridazine ring;
a pharmaceutically acceptable salt thereof, a prodrug of said compound or said salt, a solvate of said compound, said salt or said prodrug, or a polymorph of said compound, said salt, said prodrug, or said solvate.

3. The compound of claim 1 wherein $R^1$ is $(CR^7R^8)_n$-aryl, $(CR^7R^8)_n$-heteroaryl, $(CR^7R^8)_n$-(benzofused heteroaryl), or $(CR^7R^8)_n$—$(C_3$–$C_8)$cycloalkyl and n is 2, 3, 4, 5 or 6;
a pharmaceutically acceptable salt thereof, a prodrug of said compound or said salt, a solvate of said compound, said salt or said prodrug, or a polymorph of said compound, said salt, said prodrug, or said solvate.

4. The compound of claim 1 wherein $R^1$ is $(CR^7R^8)_n$-aryl or $(CR^7R^8)_n$—$(C_3$–$C_8)$cycloalkyl and n is 2 or 3;
a pharmaceutically acceptable salt thereof, a prodrug of said compound or said salt, a solvate of said compound, said salt or said prodrug, or a polymorph of said compound, said salt, said prodrug, or said solvate.

5. The compound of claim 1 wherein $R^1$ is $(CR^7R^8)_n$-aryl or $(CR^7R^8)_n$—$(C_3$–$C_8)$cycloalkyl and n is 2;
a pharmaceutically acceptable salt thereof, a prodrug of said compound or said salt, a solvate of said compound, said salt or said prodrug, or a polymorph of said compound, said salt, said prodrug, or said solvate.

6. The compound of claim 1 wherein $R^2$ is phenyl, heteroaryl, or benzofused heteroaryl, wherein each group may be optionally substituted by $(C_1$–$C_6)$alkyl, $(C_1$–$C_6)$alkoxy, halo, unsubstituted heterocycle, unsubstituted benzofused heterocycle, unsubstituted heteroaryl, unsubstituted benzofused heteroaryl, phenyl, naphthyl, $CO_2R^{11}$, $OC(O)R^{11}$ or $CONR^{11}R^{12}$;
a pharmaceutically acceptable salt thereof, a prodrug of said compound or said salt, a solvate of said compound, said salt or said prodrug, or a polymorph of said compound, said salt, said prodrug, or said solvate.

7. The compound of claim 1 wherein $R^2$ is phenyl optionally substituted by $(C_1$–$C_6)$alkyl, $(C_1$–$C_6)$alkoxy, halo, unsubstituted heterocycle, unsubstituted benzofused heterocycle, unsubstituted heteroaryl, unsubstituted benzofused heteroaryl, phenyl, naphthyl, $CO_2R^{11}$, $OC(O)R^{11}$ or $CONR^{11}R^{12}$;
a pharmaceutically acceptable salt thereof, a prodrug of said compound or said salt, a solvate of said compound, said salt or said prodrug, or a polymorph of said compound, said salt, said prodrug, or said solvate.

8. The compound of claim 1 wherein $R^2$ is phenyl optionally substituted by $(C_1-C_3)$alkyl, $(C_1-C_3)$alkoxy, F or Cl;
   a pharmaceutically acceptable salt thereof, a prodrug of said compound or said salt, a solvate of said compound, said salt or said prodrug, or a polymorph of said compound, said salt, said prodrug, or said solvate.

9. The compound of claim 1 wherein $R^3$ is $(C_1-C_6)$alkyl, $(C_2-C_6)$ alkynyl, or $(C_3-C_8)$cycloalkyl, where said alkyl, said alkynyl and said cycloalkyl groups are optionally substituted by $OR^{11}$, halo, $NHC(O)(C_1-C_6)$ alkyl, O-heterocycle, O-(benzofused heterocycle), O-heteroaryl, O-(benzofused heteroaryl), OC(O)NH-heterocycle, OC(O)NH-(benzofused heterocycle), OC(O)NH-heteroaryl, or OC(O)NH-(benzofused heteroaryl);
   a pharmaceutically acceptable salt thereof, a prodrug of said compound or said salt, a solvate of said compound, said salt or said prodrug, or a polymorph of said compound, said salt, said prodrug, or said solvate.

10. The compound of claim 1 wherein $R^3$ is $(C_2-C_3)$ alkynyl, or $(C_1-C_3)$alkyl optionally substituted by $OR^{11}$, halo, $NHC(O)-(C_1-C_6)$alkyl, O-heterocycle, O-(benzofused heterocycle), O-heteroaryl, O-(benzofused heteroaryl), OC(O)NH-heterocycle, OC(O)NH-(benzofused heterocycle), OC(O)NH-heteroaryl, or OC(O)NH-(benzofused heteroaryl);
   a pharmaceutically acceptable salt thereof, a prodrug of said compound or said salt, a solvate of said compound, said salt or said prodrug, or a polymorph of said compound, said salt, said prodrug, or said solvate.

11. The compound of claim 1 wherein $R^3$ is $(C_1-C_3)$alkyl, $CH_2CH_2OH$, $CH_2C\equiv CH$, $CH_2CH_2F$ or $CH_2CH_2OCH_3$;
   a pharmaceutically acceptable salt thereof, a prodrug of said compound or said salt, a solvate of said compound, said salt or said prodrug, or a polymorph of said compound, said salt, said prodrug, or said solvate.

12. The compound of claim 1 wherein $R^4$, $R^5$ and $R^6$ are each independently H, $(C_1-C_6)$alkoxy, $S(C_1-C_6)$alkyl, phenyl, halo, heterocycle, benzofused heterocycle, heteroaryl, benzofused heteroaryl, and $(C_1-C_6)$alkyl optionally substituted by halo or $NH_2$;
   a pharmaceutically acceptable salt thereof, a prodrug of said compound or said salt, a solvate of said compound, said salt or said prodrug, or a polymorph of said compound, said salt, said prodrug, or said solvate.

13. The compound of claim 1 wherein $R^4$ and $R^5$ are each hydrogen and $R^6$ is H, $(C_1-C_6)$alkoxy or $(C_1-C_6)$alkyl optionally substituted by halo;
   a pharmaceutically acceptable salt thereof, a prodrug of said compound or said salt, a solvate of said compound, said salt or said prodrug, or a polymorph of said compound, said salt, said prodrug, or said solvate.

14. The compound of claim 1 wherein $R^4$ and $R^5$ are each hydrogen and $R^6$ is H or $(C_1-C_6)$alkyl;
   a pharmaceutically acceptable salt thereof, a prodrug of said compound or said salt, a solvate of said compound, said salt or said prodrug, or a polymorph of said compound, said salt, said prodrug, or said solvate.

15. The compound of claim 1, 3, 4, or 5 wherein $R^7$ and $R^8$ are each independently H or $CH_3$;
   a pharmaceutically acceptable salt thereof, a prodrug of said compound or said salt, a solvate of said compound, said salt or said prodrug, or a polymorph of said compound, said salt, said prodrug, or said solvate.

16. The compound of claim 1, 3, 4, or 5 wherein $R^7$ and $R^8$ are each H;
   a pharmaceutically acceptable salt thereof, a prodrug of said compound or said salt, a solvate of said compound, said salt or said prodrug, or a polymorph of said compound, said salt, said prodrug, or said solvate.

17. The compound of claim 1 wherein $R^9$ and $R^{10}$ are each independently H or $(C_1-C_3)$alkyl optionally substituted by aryl, heterocycle, or benzofused heterocycle;
   a pharmaceutically acceptable salt thereof, a prodrug of said compound or said salt, a solvate of said compound, said salt or said prodrug, or a polymorph of said compound, said salt, said prodrug, or said solvate.

18. The compound of claim 1 wherein $R^9$ and $R^{10}$ are each H;
   a pharmaceutically acceptable salt thereof, a prodrug of said compound or said salt, a solvate of said compound, said salt or said prodrug, or a polymorph of said compound, said salt, said prodrug, or said solvate.

19. The compound of claim 1, 6, 7, 9, or 10 wherein $R^{11}$ and $R^{12}$ are each independently H or $CH_3$;
   a pharmaceutically acceptable salt thereof, a prodrug of said compound or said salt, a solvate of said compound, said salt or said prodrug, or a polymorph of said compound, said salt, said prodrug, or said solvate.

20. The compound of claim 1 wherein X is O, NH or a direct link;
   a pharmaceutically acceptable salt thereof, a prodrug of said compound or said salt, a solvate of said compound, said salt or said prodrug, or a polymorph of said compound, said salt, said prodrug, or said solvate.

21. The compound of claim 1 wherein X is O;
   a pharmaceutically acceptable salt thereof, a prodrug of said compound or said salt, a solvate of said compound, said salt or said prodrug, or a polymorph of said compound, said salt, said prodrug, or said solvate.

22. The compound of claim 1 wherein Y is O or NH;
   a pharmaceutically acceptable salt thereof, a prodrug of said compound or said salt, a solvate of said compound, said salt or said prodrug, or a polymorph of said compound, said salt, said prodrug, or said solvate.

23. The compound of claim I wherein Y is O;
   a pharmaceutically acceptable salt thereof, a prodrug of said compound or said salt, a solvate of said compound, said salt or said prodrug, or a polymorph of said compound, said salt, said prodrug, or said solvate.

24. The compound of claim 1 wherein
   $R^1$ is $(CR^7R^8)_n$-aryl or $(CR^7R^8)_n$—$(C_3-C_8)$cycloalkyl, where n is 2 and $R^7$ and $R^8$ are each H;
   $R^2$ is phenyl optionally substituted by $(C_1-C_3)$alkyl, $(C_1-C_3)$alkoxy, F or Cl;
   $R^3$ is $(C_1-C_3)$alkyl, $CH_2CH_2OH$, $CH_2C\equiv CH$, $CH_2CH_2F$ or $CH_2CH_2OCH_3$;
   $R^4$ and $R^5$ are each hydrogen;
   $R^6$ is H or $(C_1-C_6)$alkyl;
   X is O; and
   Y is O;
   a pharmaceutically acceptable salt thereof, a prodrug of said compound or said salt, a solvate of said compound, said salt or said prodrug, or a polymorph of said compound, said salt, said prodrug, or said solvate.

25. The compound of claim 1 selected from the group consisting of
   N-[6-methoxy-5-(2-methoxyphenoxy)-2-(3-pyridazinyl)-4-pyrimidinyl]-2-(1-naphthyl) ethanesulfonamide, N-[6-methoxy-5-(2-methoxyphenoxy)-2-(3-pyridazinyl)-4-pyrimidinyl]-2-(4-fluorophenyl) ethanesulfonamide, N-[6-methoxy-5-(2-methoxyphenoxy)-2-(3-pyridazinyl)-4-pyrimidinyl ]-2-cyclopentylethanesulphonamide, N-[6-methoxy-5-(2-methoxyphenoxy)-2-(3-pyridazinyl)-4-pyrimidinyl]-2-(4-carboxyphenyl) ethanesulfonamide, and N-[6-methoxy-5-(2-methoxyphenoxy)-2-(3-pyridazinyl)-4-pyrimidinyl ]-2-phenylethanesulphonamide;

a pharmaceutically acceptable salt thereof, a prodrug of said compound or said salt, a solvate of said compound, said salt or said prodrug, or a polymorph of said compound, said salt, said prodrug, or said solvate.

26. A pharmaceutical composition comprising
(a) a compound of claim 1, a pharmaceutically acceptable salt thereof, a prodrug of said compound or said salt, a solvate of said compound, said salt or said prodrug, or a polymorph of said compound, said salt, said prodrug, or said solvate; and
(b) a pharmaceutically acceptable diluent, carrier or adjuvant.

27. A method for treating a condition or disease mediated by an endothelin receptor comprising the step of administering to a patient in need of such treatment a therapeutically-effective amount of a compound of claim 1, a pharmaceutically acceptable salt thereof, a prodrug of said compound or said salt, a solvate of said compound, said salt or said prodrug, or a polymorph of said compound, said salt, said prodrug, or said solvate.

28. The method of claim 27 wherein said endothelin receptor is an $Et_A$ receptor.

29. The method of claim 27 or 28 wherein said condition or said disease is selected from the group consisting of restenosis, acute or chronic renal failure, pulmonary hypertension, systemic hypertension, benign prostatic hyperplasia, male erectile dysfunction, prostate cancer, metastatic bone cancer, congestive heart failure, stroke, subarachnoid haemorrhage, angina, atherosclerosis, cerebral and cardiac ischemia, prevention of ischaemia or reperfusion injury, cyclosporin induced nephrotoxicity, glaucoma, radiocontrast nephropathy, diabetic neuropathy, allergy, restoration of organ perfusion in haemorrhagic shock, lipoprotein lipase related disorders, chronic obstructive pulmonary disease and hyaline membrane disease in newborn.

30. A process for making a compound of formula (I)

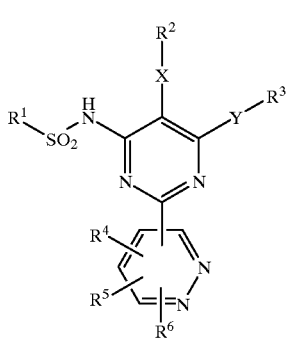

(I)

wherein $R^1$ is $(CR^7R^8)_n$—$(C_3-C_8)$cycloalkyl, $(CR^7R^8)_n$-heterocycle, $(CR^7R^8)_n$-(benzofused heterocycle), $(CR^7R^8)_n$-aryl, $NR^9R^{10}$, $(CR^7R^8)_n$- heteroaryl, and $(CR^7R^8)_n$-(benzofused heteroaryl), where $R^7$ and $R^8$ are each independently H or $(C_1-C_6)$alkyl, $R^9$ and $R^{10}$ are each independently H or $(C_1-C_6)$alkyl optionally substituted by aryl, heterocycle, benzofused heterocycle, heteroaryl, benzofused heteroaryl, or $(C_3-C_8)$cycloalkyl, and n is 2, 3, 4, 5 or 6;

$R^2$ is
(a) phenyl optionally fused with a heterocycle, benzofused heterocycle, heteroaryl, or benzofused heteroaryl,
(b) naphthyl optionally fused with a heterocycle, benzofused heterocycle, heteroaryl, or benzofused heteroaryl, or
(c) heteroaryl or benzofused heteroaryl, where groups (a), (b) and (c) are optionally substituted by $(C_1-C_6)$alkyl, $(C_1-C_6)$alkoxy, halo, unsubstituted heterocycle, unsubstituted benzofused heterocycle, unsubstituted heteroaryl, unsubstituted benzofused heteroaryl, phenyl, naphthyl, $CO_2R^{11}$, $OC(O)R^{11}$, $CONR^{11}R^{12}$, or $S(O)_pR^{11}$, where p is 0, 1, or 2, and $R^{11}$ and $R^{12}$ are each independently H or $(C_1-C_6)$alkyl;

$R^3$ is
(e) $(C_1-C_6)$alkyl,
(f) $(C_2-C_6)$alkenyl,
(g) $(C_2-C_6)$alkynyl, or
(h) $(C_3-C_8)$ cycloalkyl, where groups (e), (f), (g) and (h) are optionally substituted by $OR^{11}$, halo, $NHC(O)(C_1-C_6)$alkyl, O-heterocycle, O-(benzofused heterocycle), O-heteroaryl, O-(benzofused heteroaryl), OC(O)NH-heterocycle, OC(O)NH-(benzofused heterocycle), OC(O)NH-heteroaryl, OC(O)NH-(benzofused heteroaryl), $NH_2$, NHC(O)O-heteroaryl, NHC(O)O-(benzofused heteroaryl), NHC(O)NH-heteroaryl, or NHC(O)NH-(benzofused heteroaryl);

X is O, NH, a direct link, or $S(O)_p$, where p is 0, 1 or 2;

Y is O, NH, or $S(O)_p$, where p is 0, 1 or 2; and $R^4$, $R^5$ and $R^6$ are each independently selected from the group consisting of H, halo, heterocycle, benzofused heterocycle, heteroaryl, benzofused heteroaryl, aryl, $(C_1-C_6)$alkoxy, $(C_1-C_6)$alkyl optionally substituted by halo, $OR^9$ or $NH_2$, and $S(O)_pR^9$, where p is 0, 1 or 2; comprising the steps of:

(i) condensing a compound of formula (V) with a compound of formula (VI), where $R^{10a}$ is a $(C_1-C_6)$ alkyl or a phenyl group, to produce a compound of formula (IV)

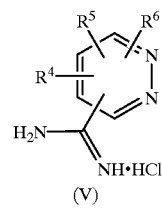 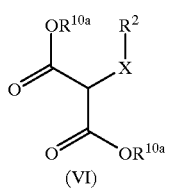

(V) (VI)

↓(i)

-continued

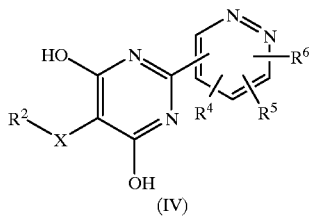
(IV)

(ii) chlorinating said compound of formula (IV) from step (i) in the presence of a base and optionally an inert solvent to produce a compound of formula (III):

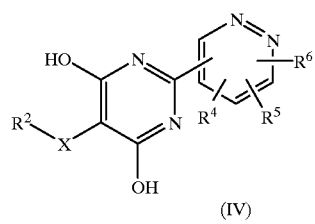
(IV)

↓(ii)

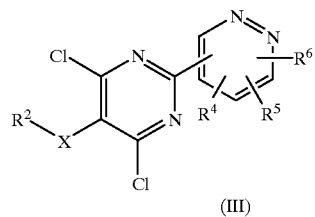
(III)

(iii) reacting said compound of formula (III) from step (ii) with a compound of formula $R^1SO_2NH_2$, in the presence of a base and heat to produce a compound of formula (II)

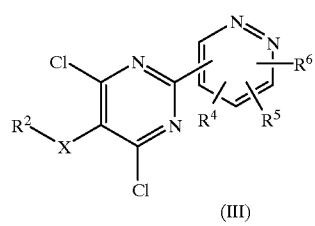
(III)

↓(iii)

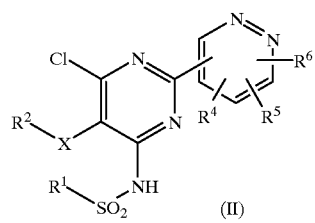
(II)

(iv) reacting said compound of formula (II) from step (iii) with a compound of formula $R^3YH$, in the presence of a base, to produce a compound of formula (I)

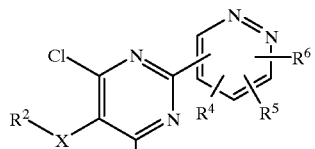
(II)

↓(iv)

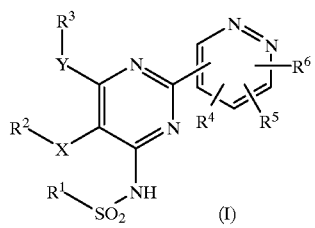
(I)

wherein $R^1$, $R^2$, $R^3$, $R^4$, $R^5$, $R^6$, X and Y for the compounds of formulae (II), (III), (IV), (V) and (VI) are as defined above for the compound of formula (I).

31. A compound of formula (I)

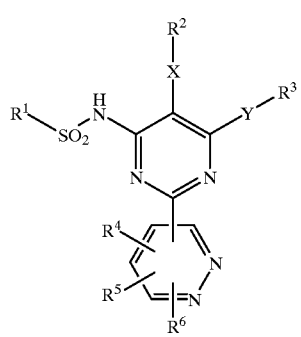
(I)

wherein $R^1$ is $(CR^7R^8)_n$—$(C_3$–$C_8)$cycloalkyl, $(CR^7R^8)_n$-heterocycle, $(CR^7R^8)_n$-(benzofused heterocycle), $(CR^7R^8)_n$-aryl, $NR^9R^{10}$, $(CR^7R^8)_n$-heteroaryl, and $(CR^7R^8)_n$-(benzofused heteroaryl), where $R^7$ and $R^8$ are each independently H or $(C_1$–$C_6)$alkyl, $R^9$ and $R^{10}$ are each independently H or $(C_1$–$C_6)$alkyl optionally substituted by aryl, heterocycle, benzofused heterocycle, heteroaryl, benzofused heteroaryl, or $(C_3$–$C_8)$cycloalkyl, and n is 2, 3, 4, 5, or 6;

$R^2$ is
(a) phenyl optionally fused with a heterocycle, benzofused heterocycle, heteroaryl, or benzofused heteroaryl,
(b) naphthyl optionally fused with a heterocycle, benzofused heterocycle, heteroaryl, or benzofused heteroaryl, or
(c) heteroaryl or benzofused heteroaryl,
where groups (a), (b) and (c) are optionally substituted by $(C_1$–$C_6)$ alkyl, $(C_1$–$C_6)$alkoxy, halo, unsubstituted heterocycle, unsubstituted benzofused heterocycle, unsubstituted heteroaryl, unsubstituted benzofused heteroaryl, phenyl, naphthyl, $CO_2R^{11}$, $OC(O)R^{11}$, $CONR^{11}R^{12}$, or $S(O)_pR^{11}$, where p is 0, 1, or 2, and $R^{11}$ and $R^{12}$ are each independently H or $(C_1$–$C_6)$alkyl;

R³ is
- (e) (C₁–C₆)alkyl,
- (f) (C₂–C₆)alkenyl,
- (g) (C₂–C₆)alkynyl, or
- (h) (C₃–C₈)cycloalkyl, where groups (e), (f), (g) and (h) are optionally substituted by OR¹¹, halo, NHC(O)(C₁–C₆)alkyl, O-heterocycle, O-(benzofused heterocycle), O-heteroaryl, O-(benzofused heteroaryl), OC(O)NH-heterocycle, OC(O)NH-(benzofused heterocycle), OC(O)NH-heteroaryl, OC(O)NH-(benzofused heteroaryl), NH₂, NHC(O)O-heteroaryl, NHC(O)O-(benzofused heteroaryl), NHC(O)NH-heteroaryl, or NHC(O)NH-(benzofused heteroaryl);

X is O, NH, a direct link, or S(O)$_p$, where p is 0, 1 or 2;
Y is O, NH, or S(O)$_p$, where p is 0, 1 or 2; and
R⁴, R⁵ and R⁶ are each independently selected from the group consisting of H, halo, heterocycle, benzofused heterocycle, heteroaryl, benzofused heteroaryl, aryl, (C₁–C₆)alkoxy, (C₁–C₆)alkyl optionally substituted by halo, OR⁹ or NH₂, and S(O)$_p$R⁹, where p is 0, 1 or 2, and R⁹ is H or (C₁–C₆)alkyl optionally substituted by aryl, heterocycle, benzofused heterocycle, heteroaryl, benzofused heteroaryl, or (C₃–C₈)cycloalkyl;

prepared by the process of claim 30.

32. A compound of formula (IV)

(IV)

wherein
R² is
- (a) phenyl optionally fused with a heterocycle, benzofused heterocycle, heteroaryl, or benzofused heteroaryl,
- (b) naphthyl optionally fused with a heterocycle, benzofused heterocycle, heteroaryl, or benzofused heteroaryl, or
- (c) heteroaryl or benzofused heteroaryl, where groups (a), (b) and (c) are optionally substituted by (C₁–C₆) alkyl, (C₁–C₆)alkoxy, halo, unsubstituted heterocycle, unsubstituted benzofused heterocycle, unsubstituted heteroaryl, unsubstituted benzofused heteroaryl, phenyl, naphthyl, CO₂R¹¹, OC(O)R¹¹, CONR¹¹R¹², or S(O)$_p$R¹¹, where p is 0, 1, or 2, and R¹¹ and R¹² are each independently H or (C₁–C₆)alkyl;

X is O, NH, a direct link, or S(O)$_p$, where p is 0, 1 or 2; and
R⁴, R⁵ and R⁶ are each independently selected from the group consisting of H, halo, heterocycle, benzofused heterocycle, heteroaryl, benzofused heteroaryl, aryl, (C₁–C₆)alkoxy, (C₁–C₆)alkyl optionally substituted by halo, OR⁹ or NH₂, and S(O)$_p$R⁹, where p is 0, 1 or 2, and R⁹ is H or (C₁–C₆)alkyl optionally substituted by aryl, heterocycle, benzofused heterocycle, heteroaryl, benzofused heteroaryl, or (C₃–C₈)cycloalkyl.

33. A compound of formula (III)

(III)

wherein
R² is
- (a) phenyl optionally fused with a heterocycle, benzofused heterocycle, heteroaryl, or benzofused heteroaryl,
- (b) naphthyl optionally fused with a heterocycle, benzofused heterocycle, heteroaryl, or benzofused heteroaryl, or
- (c) heteroaryl or benzofused heteroaryl, where groups (a), (b) and (c) are optionally substituted by (C₁–C₆) alkyl, (C₁–C₆)alkoxy, halo, unsubstituted heterocycle, unsubstituted benzofused heterocycle, unsubstituted heteroaryl, unsubstituted benzofused heteroaryl, phenyl, naphthyl, CO₂R¹¹, OC(O)R¹¹, CONR¹¹R¹², or S(O)$_p$R¹¹, where p is 0, 1, or 2, and R¹¹ and R¹² are each independently H or (C₁–C₆)alkyl;

X is O, NH, a direct link, or S(O)$_p$, where p is 0, 1 or 2; and
R⁴, R⁵ and R⁶ are each independently selected from the group consisting of H, halo, heterocycle, benzofused heterocycle, heteroaryl, benzofused heteroaryl, aryl, (C₁–C₆)alkoxy, (C₁–C₆)alkyl optionally substituted by halo, OR⁹ or NH₂, and S(O)$_p$R⁹, where p is 0, 1 or 2, and R⁹ is H or (C₁–C₆)alkyl optionally substituted by aryl, heterocycle, benzofused heterocycle, heteroaryl, benzofused heteroaryl, or (C₃–C₈)cycloalkyl.

34. A compound of formula (II)

(II)

wherein
R¹ is (CR⁷R⁸)$_n$—(C₃–C₈)cycloalkyl, (CR⁷R⁸)$_n$-heterocycle, (CR⁷R⁸)$_n$-(benzofused heterocycle), (CR⁷R⁸)$_n$-aryl, NR⁹R¹⁰, (CR⁷R⁸)$_n$-heteroaryl, and (CR⁷R⁸)$_n$-(benzofused heteroaryl), where R⁷ and R⁸ are each independently H or (C₁–C₆)alkyl, R⁹ and R¹⁰ are each independently H or (C₁–C₆)alkyl optionally substituted by aryl, heterocycle, benzofused heterocycle, heteroaryl, benzofused heteroaryl, or (C₃–C₈)cycloalkyl, and n is 2–6;

R² is
- (a) phenyl optionally fused with a heterocycle, benzofused heterocycle, heteroaryl, or benzofused heteroaryl,
- (b) naphthyl optionally fused with a heterocycle, benzofused heterocycle, heteroaryl, or benzofused heteroaryl, or
- (c) heteroaryl or benzofused heteroaryl, where groups (a), (b) and (c) are optionally substituted by ($C_1$–$C_6$) alkyl, ($C_1$–$C_6$)alkoxy, halo, unsubstituted heterocycle, unsubstituted benzofused heterocycle, unsubstituted heteroaryl, unsubstituted benzofused heteroaryl, phenyl, naphthyl, $CO_2R^{11}$, $OC(O)R^{11}$, $CONR^{11}R^{12}$, or $S(O)_pR^{11}$, where p is 0, 1, or 2, and $R^{11}$ and $R^{12}$ are each independently H or ($C_1$–$C_6$)alkyl;

X is O, NH, a direct link, or $S(O)_p$, where p is 0, 1 or 2; and $R^4$, $R^5$ and $R^6$ are each independently selected from the group consisting of H, halo, heterocycle, benzofused heterocycle, heteroaryl, benzofused heteroaryl, aryl, ($C_1$–$C_6$)alkoxy, ($C_1$–$C_6$)alkyl optionally substituted by halo, $OR^9$ or $NH_2$, and $S(O)_pR^9$, where p is 0, 1 or 2, and $R^9$ is H or ($C_1$–$C_6$)alkyl optionally substituted by aryl, heterocycle, benzofused heterocycle, heteroaryl, benzofused heteroaryl, or ($C_3$–$C_8$)cycloalkyl.

35. A compound of formula (V)

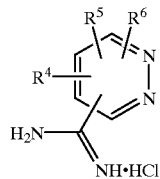

(V)

wherein $R^4$, $R^5$ and $R^6$ are each independently selected from the group consisting of H, halo, heterocycle, benzofused heterocycle, heteroaryl, benzofused heteroaryl, aryl, ($C_1$–$C_6$)alkoxy, ($C_1$–$C_6$)alkyl optionally substituted by halo, $OR^9$ or $NH_2$, and $S(O)_pR^9$, where p is 0, 1 or 2, and $R^9$ is H or ($C_1$–$C_6$)alkyl optionally substituted by aryl, heterocycle, benzofused heterocycle, heteroaryl, benzofused heteroaryl, or ($C_3$–$C_8$)cycloalkyl.

* * * * *